US010102337B2

(12) United States Patent
Scolnick et al.

(10) Patent No.: US 10,102,337 B2
(45) Date of Patent: Oct. 16, 2018

(54) DIGITAL MEASUREMENTS FROM TARGETED SEQUENCING

(71) Applicant: Nugen Technologies, Inc., San Carlos, CA (US)

(72) Inventors: Jonathan Scolnick, San Francisco, CA (US); Benjamin Schroeder, San Mateo, CA (US); Douglas Amorese, Los Altos, CA (US); Stephanie C. Huelga, Belmont, CA (US)

(73) Assignee: NuGEN Technologies, Inc., San Carlos, CA (US)

( * ) Notice: Subject to any disclaimer, the term of this patent is extended or adjusted under 35 U.S.C. 154(b) by 554 days.

(21) Appl. No.: 14/820,250

(22) Filed: Aug. 6, 2015

(65) Prior Publication Data

US 2016/0203259 A1    Jul. 14, 2016

Related U.S. Application Data

(60) Provisional application No. 62/034,043, filed on Aug. 6, 2014.

(51) Int. Cl.
| | | |
|---|---|---|
| *G06F 19/22* | (2011.01) | |
| *C12Q 1/68* | (2018.01) | |
| *C12Q 1/6886* | (2018.01) | |
| *G06F 19/28* | (2011.01) | |
| *C12Q 1/6806* | (2018.01) | |
| *C12Q 1/689* | (2018.01) | |

(52) U.S. Cl.
CPC .......... *G06F 19/22* (2013.01); *C12Q 1/6806* (2013.01); *C12Q 1/689* (2013.01); *C12Q 1/6886* (2013.01); *G06F 19/28* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,925,065 A | 5/1990 | Golias | |
| 5,384,242 A | 1/1995 | Oakes | |
| 5,750,341 A | 5/1998 | Macevicz | |
| 5,969,119 A | 10/1999 | Macevicz | |
| 6,110,709 A | 8/2000 | Ausubel et al. | |
| 6,225,109 B1 | 5/2001 | Juncosa et al. | |
| 6,251,639 B1 | 6/2001 | Kurn | |
| 6,287,766 B1 | 9/2001 | Nolan et al. | |
| 6,306,597 B1 | 10/2001 | Macevicz | |
| 6,449,562 B1 | 9/2002 | Chandler et al. | |
| 7,170,050 B2 | 1/2007 | Turner et al. | |
| 7,211,390 B2 | 5/2007 | Rothberg et al. | |
| 7,244,559 B2 | 7/2007 | Rothberg et al. | |
| 7,244,567 B2 | 7/2007 | Chen et al. | |
| 7,264,929 B2 | 9/2007 | Rothberg et al. | |
| 7,276,720 B2 | 10/2007 | Ulmer | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,323,305 B2 | 1/2008 | Leamon et al. | |
| 7,335,762 B2 | 2/2008 | Rothberg et al. | |
| 7,361,468 B2 | 4/2008 | Liu et al. | |
| 7,405,281 B2 | 7/2008 | Xu et al. | |
| 7,414,117 B2 | 8/2008 | Saito et al. | |
| 7,462,452 B2 | 12/2008 | Williams et al. | |
| 7,462,468 B1 | 12/2008 | Williams et al. | |
| 7,476,503 B2 | 1/2009 | Turner et al. | |
| 7,476,504 B2 | 1/2009 | Turner | |
| 7,491,498 B2 | 2/2009 | Lapidus et al. | |
| 7,501,245 B2 | 3/2009 | Quake et al. | |
| 7,704,687 B2 | 4/2010 | Wang et al. | |
| 8,209,130 B1 | 6/2012 | Kennedy et al. | |
| 9,248,076 B2 | 2/2016 | Sullivan et al. | |
| 2003/0211616 A1 | 11/2003 | Leong | |
| 2006/0024678 A1 | 2/2006 | Buzby | |
| 2006/0024711 A1 | 2/2006 | Lapidus et al. | |
| 2006/0286566 A1 | 12/2006 | Lapidus et al. | |
| 2007/0263045 A1 | 11/2007 | Okazawa | |
| 2008/0087826 A1 | 4/2008 | Harris et al. | |

(Continued)

FOREIGN PATENT DOCUMENTS

| | | |
|---|---|---|
| CA | 2444926 A1 | 11/2002 |
| EP | 0329822 B1 | 6/1994 |

(Continued)

OTHER PUBLICATIONS

Shiroguchi et al. Digital RNA sequencing minimizes sequence-dependent bias and amplification noise with optimized singl-molecule barcodes Proceedings of the National Academy of Sciences USA vol. 109, pp. 1347-1352 (Year: 2012).*
International Search Report & Written Opinion dated Jan. 6, 2016 for PCT/US15/44065.
Ovation Target Enrichment System [online], NuGen, Jul. 2014 [retrieved on Dec. 10, 2015], Retrieved from the Internet: <URL: http://www.nugen.com/sites/default/files/M01383_v1%20-%A20Data%20Sheet,%200vation%20Target%20Enrichment%20System.pdf>; pp. 1-4; p. 2.
Bod I, K et al. Comparison of Commercially Available Target Enrichment Methods for Next-Generation Sequencing. Journal of Biomolecular Techniques. 2013, vol. 24, pp. 73-86; p. 78, second column, first paragraph; Table 3; figure 1. DOI: 10.7171/jbt.13-2402-002.

(Continued)

*Primary Examiner* — John S Brusca
(74) *Attorney, Agent, or Firm* — Brown Rudnick LLP; Thomas C. Meyers

(57) ABSTRACT

Disclosed herein are methods, compositions and kits for quantitating one or more specific nucleic acids within a plurality of nucleic acids. In some embodiments, a sequencing library is constructed from enriched probe extension products specific for the specific nucleic acids and sequenced. In some embodiments, the resulting reads are used for removing duplicate reads. In some embodiments, counting of verified probes is used to quantitate or determine the number of specific nucleic acid molecules in the starting nucleic acid sample.

18 Claims, 16 Drawing Sheets

(56) References Cited

U.S. PATENT DOCUMENTS

| | | |
|---|---|---|
| 2008/0103058 A1 | 5/2008 | Siddiqi |
| 2008/0206764 A1 | 8/2008 | Williams et al. |
| 2008/0213770 A1 | 9/2008 | Williams et al. |
| 2008/0217246 A1 | 9/2008 | Benn et al. |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0061439 A1 | 3/2009 | Buzby |
| 2009/0068655 A1 | 3/2009 | Williams |
| 2009/0233802 A1 | 9/2009 | Bignell et al. |
| 2012/0071331 A1 | 3/2012 | Casbon et al. |
| 2012/0107811 A1 | 5/2012 | Kelso et al. |
| 2012/0208705 A1 | 8/2012 | Steemers et al. |
| 2012/0220494 A1 | 8/2012 | Samuels et al. |
| 2013/0005585 A1 | 1/2013 | Anderson et al. |
| 2013/0231253 A1* | 9/2013 | Amorese ............ C12N 15/1068 506/2 |
| 2015/0101595 A1 | 4/2015 | Hancock et al. |
| 2015/0299784 A1 | 10/2015 | Fan et al. |
| 2015/0299812 A1 | 10/2015 | Talasaz |
| 2016/0203259 A1 | 7/2016 | Scolnick et al. |
| 2016/0220994 A1 | 8/2016 | Wright |
| 2016/0296930 A1 | 10/2016 | Matear et al. |

FOREIGN PATENT DOCUMENTS

| | | |
|---|---|---|
| EP | 0667393 A2 | 8/1995 |
| EP | 1071811 B1 | 3/2002 |
| EP | 0843735 B1 | 7/2002 |
| EP | 2272976 A1 | 1/2011 |
| EP | 2322612 A1 | 5/2011 |
| EP | 2451973 A1 | 5/2012 |
| EP | 2511381 A1 | 10/2012 |
| WO | 92/07951 A1 | 5/1992 |
| WO | 93/18052 A1 | 9/1993 |
| WO | 94/16090 A1 | 7/1994 |
| WO | 96/40998 A1 | 12/1996 |
| WO | 97/12061 A1 | 4/1997 |
| WO | 97/25416 A2 | 7/1997 |
| WO | 98/06736 A1 | 2/1998 |
| WO | 98/38296 A1 | 9/1998 |
| WO | 98/044151 A1 | 10/1998 |
| WO | 99/10540 A1 | 3/1999 |
| WO | 99/11819 A1 | 3/1999 |
| WO | 99/42618 A1 | 8/1999 |
| WO | 00/08208 A2 | 2/2000 |
| WO | 2000/09756 A1 | 2/2000 |
| WO | 00/018957 A1 | 4/2000 |
| WO | 00/39345 A1 | 7/2000 |
| WO | 00/52191 A1 | 9/2000 |
| WO | 2000/55364 A2 | 9/2000 |
| WO | 00/70039 A1 | 11/2000 |
| WO | 01/20035 A2 | 3/2001 |
| WO | 01/23613 A1 | 4/2001 |
| WO | 01/46464 A1 | 6/2001 |
| WO | 01/57248 A2 | 8/2001 |
| WO | 01/64952 A2 | 9/2001 |
| WO | 02/00938 A2 | 1/2002 |
| WO | 02/28876 A2 | 4/2002 |
| WO | 02/29117 A2 | 4/2002 |
| WO | 02/36821 A2 | 5/2002 |
| WO | 02/48402 A2 | 6/2002 |
| WO | 02/060318 A2 | 8/2002 |
| WO | 02/072772 A2 | 9/2002 |
| WO | 02/072773 A2 | 9/2002 |
| WO | 02/081753 A1 | 10/2002 |
| WO | 02/090584 A2 | 11/2002 |
| WO | 2003/002736 A2 | 1/2003 |
| WO | 2003/012118 A1 | 2/2003 |
| WO | 03/027259 A2 | 4/2003 |
| WO | 03/078645 A2 | 9/2003 |
| WO | 03/083435 A2 | 10/2003 |
| WO | 03/106642 A2 | 12/2003 |
| WO | 04/011665 A2 | 2/2004 |
| WO | 2004/092418 A2 | 10/2004 |
| WO | 2005/038427 A2 | 4/2005 |
| WO | 2005/065321 A2 | 7/2005 |
| WO | 2006/081222 A2 | 8/2006 |
| WO | 2006/086668 A2 | 8/2006 |
| WO | 2007/018601 A1 | 2/2007 |
| WO | 2007/019444 A2 | 2/2007 |
| WO | 2007/030759 A2 | 3/2007 |
| WO | 2007/052006 A1 | 5/2007 |
| WO | 2007/057652 A1 | 5/2007 |
| WO | 2007/136717 A1 | 11/2007 |
| WO | 2008/005459 A2 | 1/2008 |
| WO | 2008/015396 A2 | 2/2008 |
| WO | 2008/033442 A2 | 3/2008 |
| WO | 2008/093098 A2 | 8/2008 |
| WO | 2008/115185 A2 | 9/2008 |
| WO | 2009/053039 A1 | 4/2009 |
| WO | 2009/102878 A2 | 8/2009 |
| WO | 2009/102896 A2 | 8/2009 |
| WO | 2009/112844 A1 | 9/2009 |
| WO | 2009/117698 A2 | 9/2009 |
| WO | 2009/120372 A2 | 10/2009 |
| WO | 2009/120374 A2 | 10/2009 |
| WO | 2010/003153 A2 | 1/2010 |
| WO | 2010/030683 A1 | 3/2010 |
| WO | 2010/039991 A2 | 4/2010 |
| WO | 2010/063711 A1 | 6/2010 |
| WO | 2010/064893 A1 | 6/2010 |
| WO | 2010/085715 A1 | 7/2010 |
| WO | 2010/091246 A1 | 8/2010 |
| WO | 2010/115154 A1 | 10/2010 |
| WO | 2010/129937 A2 | 11/2010 |
| WO | 2011/003630 A1 | 1/2011 |
| WO | 2011/009941 A1 | 1/2011 |
| WO | 2011/019964 A1 | 2/2011 |
| WO | 2011/032053 A1 | 3/2011 |
| WO | 2011/053987 A1 | 5/2011 |
| WO | 2011/151777 A1 | 12/2011 |
| WO | 2011/156529 A2 | 12/2011 |
| WO | 2012/013932 A1 | 2/2012 |
| WO | 2012/061832 A1 | 5/2012 |
| WO | 2012/054873 A3 | 8/2012 |
| WO | 2012/103154 A1 | 8/2012 |
| WO | 2013/059740 A1 | 4/2013 |
| WO | 2013/059746 A1 | 4/2013 |
| WO | 2013/112923 A1 | 8/2013 |
| WO | 2013/130512 A3 | 10/2013 |
| WO | 2013/177220 A1 | 11/2013 |
| WO | 2013/190441 A2 | 12/2013 |
| WO | 2013/191775 A2 | 12/2013 |
| WO | 2014/039556 A1 | 3/2014 |
| WO | 2014/082032 A1 | 5/2014 |
| WO | 2013/138510 A9 | 7/2014 |
| WO | 2014/144092 A1 | 9/2014 |
| WO | 2014/150931 A1 | 9/2014 |
| WO | 2015/031691 A1 | 3/2015 |
| WO | 2015/131107 A1 | 9/2015 |

OTHER PUBLICATIONS

Bellos, 2014, cnvCapSeq: detecting copy number variation in long-range targeted resequencing data, Nucleic Acids Res 42(20):e158.
Benson, 2013, Genbank, Nucl Acids Res 41:D36-D42.
Blomquist, 2013, Targeted RNA-Sequencing with Competitive Multiplex-PCR Amplicon Libraries, PLOS ONE 8(11):e79120.
Eminaga, 2013, Quantification of microRNA Expression with Next-Generation Sequencing, Unit 4.17 in Current Protocols in Molecular Biology, Wiley, New York, NY (14 pages).
Grothues, 1993, PCR amplification of megabase DNA with tagged random primers (T-PCR), Nucl Acids Res 21:1321-1322.
Illumina, 2011, TruSeq RNA and DNA Sample Preparation Kits v2, 1-15 Illumina, dated 27 Apr. 27, 2011 (4 pages).
International Search Report and Written Opinion dated Mar. 5, 2015, in international patent application PCT/US2014/065530, filed Nov. 13, 2014 (12 pages).
Jiang, 2015, CODEX: a normalization and copy number variation detection method for whole exome sequencing, Nucleic Acids Res 43(6):e39.

(56) References Cited

OTHER PUBLICATIONS

Krumm, 2012, Copy number variation detection and genotyping from exome sequence data, Genome Res 22(8):1525-1532.
Langmead, 2009, Ultrafast and memory-efficient alignment of short DNA sequences to the human genome, Genome Biol 10:R25.
Li, 2012, CONTRA: copy number analysis for targeted resequencing, Bioinformatics 28(10):1307-1313.
Liu 2008, Sequence space coverage, entropy of genomes and the potential to detect non-human DNA in human samples, BMC Genomics 9(509):1-17.
Ma, 2015, Quantitative Analysis of Copy Number Variants Based on Real-Time LightCycler PCR, Curr Protoc Hum Genet 80:7.21.1-7.23.8.
Margulies, 2005, Genorne sequencing in open microfabricated high density picoliter reactors, Nature 437(7057):376-380.
McCloskey, 2007, Encoding PCR products with batch-stamps and barcodes, Biochem Genet 45:761-767.
Myers, 2013, Protocol for Creating Multiplexed miRNA Libraries for Use in Illumina Sequencing, Myers lab microRNA-seq Protocol, Hudson Alpha Institute for Biotechnology web site, dated May 2, 2013, (15 pages).
NuGEN, 2014, User Guide Ovation Target Enrichment System, NuGEN Technologies Inc., San Carlos, CA (45 pages).
Plagnol, 2012, A robust model for read count data in exome sequencing experiments and implications for copy number viariant calling, Bioinformatics 28(21):2747-2754.
Querfurth, 2012, Creation and application of immortalized bait libraries for targeted enrichment and next-generation sequencing, Biotechniques 52(6):375-380.
Sathirapongsasuti, 2011, Exome sequencing-based copy-number variation and loss of heterozygosity detection: ExomeCNV, Bioinformatics 27(19):2648-2654.
Schiemer, 2011, Illumina TruSeq Adapters Demystified,Tufts University Core Facility XP055357867 (5 pages).
Soni, 2007, Progress toward ultrafast DNA sequencing using solid-state nanopores, Clin Chem 53(11):1996-2001.
Stratagene, 1998, Gene characterization kits, Stratagene Catalog, p. 39 (2 pages).
Supplementary European search report and opinion dated Jan. 30, 2018, for European patent application No. 15830393.3 (6 pages).
Trapnell, 2010, Transcript assembly and quantification by RNA-Seq reveals unannotated transcripts and isoform switching during cell differentiation, Nat Biotech 28:511-515.
Trapnell, 2013, Differential analysis of gene regulation at transcript resolution with RNA-seq, Nat Biotech 31:46-53.
Walker, 1992, Strand displacement amplification—an isothermal, in vitro DNA amplification technique, Nucl Acids Res 20(7):1691-1696.
Westin 2000, Anchored multiplex amplification on a microelectronic chip array, Nat Biotech 18:199-204.
Xi, 2011, Copy number variation detection in whole-genome sequencing data using the Bayesian information criterion, PNAS 108(46):e1128-e1136.

\* cited by examiner

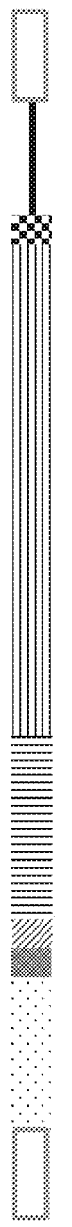
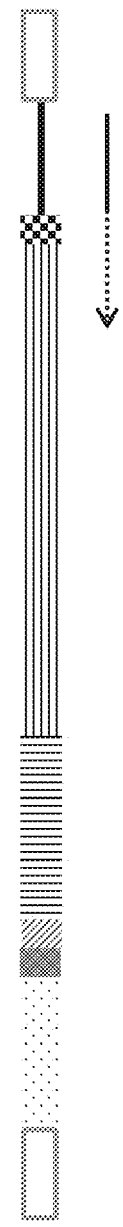
Figure 7
Figure 7A
Figure 7B
Figure 7C

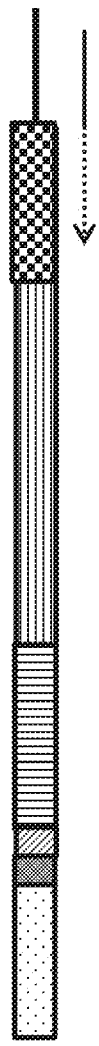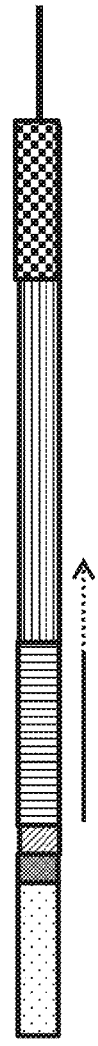
Figure 8
Figure 8A
Figure 8B
Figure 8C

DIGITAL MEASUREMENTS FROM TARGETED SEQUENCING

CROSS-REFERENCE TO RELATED APPLICATIONS

This application claims the benefit of U.S. Provisional Application Ser. No. 62/034,043, filed Aug. 6, 2014, which is herein incorporated by reference in its entirety for all purposes.

FIELD OF THE INVENTION

The present teachings relate to the use of targeted nucleic acid sequencing that result in digital measurements for gene expression and copy number variation.

BACKGROUND OF THE INVENTION

Molecular methods that provide digital counts of a specific nucleic acid(s) are of interest to the research and clinical community. These methods can be used to discretely measure gene expression (digital gene expression or DGE) or copy number variation (CNV). The precision measurements that can be obtained by digital readouts provides higher confidence in data compared to microarray technology and allows researchers to identify smaller differences between samples or similarly, differences within subsets of cells such as in a tumor biopsy as well as determining cell to cell variations.

However there is still a need for different methods for selective target quantitation that allow for high throughput analysis of transcriptome and genomic regions of interest without specialized instrumentation. The methods, compositions and kits disclosed herein fulfill these needs and provide related advantages.

SUMMARY OF THE INVENTION

In one aspect, disclosed is a method for quantitating a plurality of specific nucleic acids within a plurality of nucleic acids comprising: a. generating a sequencing library of a plurality of probe extension products, wherein each probe extension product can be derived from extending a probe complementary to and hybridized to a probe target region within a specific nucleic acid sequence; b. sequencing the library comprising the plurality of probe extension products to generate sequence data for the plurality of probe extension products; and c. counting each of the aligned sequences, wherein the number of alignments indicates the quantity of each of the corresponding specific nucleic acid molecules, within the plurality of nucleic acids.

In one aspect, disclosed in a method for quantitating a plurality of specific nucleic acid molecules in a composition comprising: a. generating a plurality of probe extension products, wherein each probe extension product comprises a probe sequence that is complementary to a probe target region within a specific nucleic acid molecule; b. sequencing the plurality of probe extension products to generate a sequence for each of the plurality of probe extension products; c. aligning the sequence of each of the plurality of probe extension products to a reference sequence database, wherein the reference sequence database comprises probe sequences; and d. determining the number of alignments for the sequence of each probe extension product with a sequence in the reference sequence database, wherein the number of alignments indicates the quantity of each of the specific nucleic acid molecule that the probe of the probe extension product is complementary to.

In one aspect, disclosed is a method for quantitating a plurality of specific nucleic acids within a plurality of nucleic acids comprising: a. generating a sequencing library of a plurality of probe extension products, wherein each probe extension product comprises a first adapter attached to the 5' end of each probe extension product, wherein each probe extension product can be derived from extending a probe complementary to and hybridized to a probe target region within a specific nucleic acid sequence; b. sequencing the library to generate sequence data for the plurality of probe extension products; and c. identifying the presence of the probe sequence within the sequence data and counting each probe sequence within the plurality of probe extension products, wherein the number of probes counted indicates the quantity of each of the plurality of specific nucleic acid molecules within the plurality of nucleic acids.

In one aspect, disclosed is a method for quantitating a plurality of specific nucleic acid molecules comprising: a. generating a plurality of probe extension products, wherein each probe extension product comprises (i) a first adapter, and (ii) a probe sequence complementary to a probe target region within a specific nucleic acid molecule; b. sequencing the plurality of probe extension products to generate sequence data comprising a sequence for each of the plurality of probe extension products; c. identifying the presence of the probe sequence of each probe extension product within the sequence data; and d. determining the number of each of the probe sequences within the plurality of probe extension products, wherein the number of each of the probe sequences indicates the quantity of each of the plurality of specific nucleic acid molecules to which each of the probes sequences is complementary to.

In one aspect, disclosed is a method for quantitating a plurality of specific nucleic acids within a plurality of nucleic acids comprising: a. appending a first adaptor sequence to a 5' end of a plurality of nucleic acids; b. hybridizing a plurality of probes, wherein each probe is complementary to a probe target region within a specific nucleic acid within the plurality of specific nucleic acids; c. extending each probe into the appended first adaptor sequence to generate a plurality of probe extension products having the first adaptor sequence and a second adaptor sequence; d. generating a sequencing library comprising the plurality of probe extension products; e. sequencing the library, wherein sequence data is obtained for each of the plurality of probe extension products; f. aligning the sequence data for each of the plurality of probe extension products to a pre-determined sequence within a reference copy of a probe database, wherein said pre-determined sequence is specific to each probe; and g. counting each probe sequence aligned to its pre-determined sequence, wherein the number of counts for each probe specific for its specific nucleic acid indicates the quantity of each of the specific nucleic acids molecules within the plurality of specific nucleic acids within the plurality of nucleic acids.

In one aspect, disclosed is a method for quantifying a plurality of specific nucleic acid molecules within a plurality of nucleic acid molecules comprising: a. appending a first adaptor sequence to a 5' end to each of a plurality of nucleic acid molecules; b. hybridizing a plurality of probes to the plurality of specific nucleic acid molecules, wherein each probe is complementary to a probe target region within a specific nucleic acid molecule; c. extending each probe into the appended first adaptor sequence to generate a plurality of probe extension products having the first adaptor sequence and a second adaptor sequence to produce a plurality of probe extension products; d. sequencing the plurality of probe extension products to generate sequence data for each of the plurality of probe extension products; e. aligning the sequence for each of the plurality of probe extension products to a pre-determined sequence within a reference copy of a probe database, wherein said pre-determined sequence is specific to each probe; and f determining the number of each probe sequence aligned to its pre-determined sequence, wherein the number indicates the quantity of the specific nucleic acids molecule to which the probe is complementary to.

In one aspect, disclosed is a method for quantitating a plurality of specific nucleic acids within a plurality of nucleic acids comprising: a. extending a plurality of hybridized probes, wherein each probe is complementary to a probe target region within a specific nucleic acid within the plurality of specific nucleic acids and each probe has a 5' first adaptor; b. appending a second adaptor sequence to the double-stranded end of the plurality of probe extension products to generate a sequencing library; c. sequencing the library, wherein sequence data can be obtained for each of the plurality of probe extension products; and d. counting each probe sequence corresponding to each probe target region, wherein the number of counts for each probe specific for its specific nucleic acid indicates the quantity of each of the specific nucleic acids molecules within the plurality of specific nucleic acids within the plurality of nucleic acids.

In one aspect, disclosed is a method for quantitating a plurality of specific nucleic acid molecules comprising: a. extending a plurality of probes, wherein each probe is hybridized to a probe target region within a specific nucleic acid molecule within the plurality of specific nucleic acid molecules and each probe has a first adaptor at its 5' end to generate a plurality of extension products; b. appending a second adaptor to the double-stranded end of the plurality of probe extension products; c. sequencing the plurality of probe extension products to generate sequence data for each of the probe extension products; and d. determining the number of each probe that hybridized to a probe target region, wherein the number indicates the quantity of each of the specific nucleic acid molecules comprising the probe target region.

In one aspect, disclosed is a method for quantitating a plurality of specific nucleic acids within a plurality of nucleic acids comprising: a. hybridizing a plurality of probes, wherein each probe is complementary to a probe target region within a specific nucleic acid within the plurality of specific nucleic acids and each probe has a 5' first adaptor; b. extending each probe to generate a plurality of probe extension products having the first adaptor sequence; c. appending a second adaptor sequence to the double-stranded end of the plurality of probe extension products; d. generating a sequencing library comprising the plurality of probe extension products; e. sequencing the library, wherein sequence data can be obtained for each of the plurality of probe extension products; f. aligning the sequence data for each of the plurality of probe extension products to a pre-determined sequence within a probe database, wherein said pre-determined sequence is specific to each probe; and g. counting each probe sequence aligned to the probe target region, wherein the number of counts for each probe specific for its specific nucleic acid indicates the quantity of each of the specific nucleic acids molecules within the plurality of specific nucleic acids within the plurality of nucleic acids.

In one aspect, disclosed is a method for quantitating a plurality of specific nucleic acid molecules in a composition comprising: a. hybridizing a plurality of probes to a probe target region within a specific nucleic acid molecule, wherein each probe has a first adaptor at its 5' end; b. extending each probe to generate a plurality of probe extension products comprising the first adaptor sequence; c. appending a second adaptor sequence to the double-stranded end of the plurality of probe extension products; d. sequencing the plurality of probe extension products to generate sequence for each of the plurality of probe extension products; e. aligning the sequence for each of the plurality of probe extension products to a pre-determined sequence within a probe database, wherein said probe database comprises a plurality of pre-determined sequences, wherein each pre-determined sequence is specific to a probe; and f. determining the number of alignments for the sequence of each probe extension product to a pre-determined sequence within the sequencing database, wherein the number of alignments indicates the quantity of each of the specific nucleic acids molecules to which the probe hybridizes to.

In some embodiments, the sequence data or sequenced plurality of probe extension products comprise at least one of a forward read, an index read and a reverse read. In some embodiments, the reverse read comprises the probe target region. In some embodiments, specificity that each probe has annealed to its respective probe target region sequence within its respective specific nucleic acid can be verified. In some embodiments, the sequence data or sequenced plurality of probe extension products can be mapped to coordinates of a genome or a transcriptome database and/or the sequence data or sequenced plurality of probe extension products can be aligned to a reference copy of a probe database to verify intended probe annealing and extension. In some embodiments, the sequence data or sequenced plurality of probe extension products can be mapped to coordinates of a genome or a transcriptome database. In some embodiments, the reverse read or the forward read comprises the probe target region. In some embodiments, the sequence data or sequenced plurality of probe extension products for the forward and reverse reads can be mapped for the plurality of specific nucleic acids and the sequence data or sequenced plurality of probe extension products for the index read can identify at least one of the barcode sequence and the n-random sequence. In some embodiments, the combination of the forward read map coordinates and the index read n-random bases determine PCR duplicates for each probe extension product and sequences having the same forward read coordinates and the same n-random base sequence can be identified as duplicates, consolidated and counted as a single specific nucleic acid molecule; and wherein sequences with the same forward read coordinates but different n-random base sequences can be each counted as a distinct specific nucleic acid molecule.

In some embodiments, the forward reads and corresponding reverse reads can be pair end aligned. In some embodiments, following duplicate consolidation, the number of reverse reads or forward reads counted for each probe sequence generates a value that represents the number of molecules for each starting specific nucleic acid molecule within the plurality of specific nucleic acids. In some embodiments, the genome is selected from the group consisting of a mammalian, bacterial, viral, rickettsial or plant genome or transcriptome. In some embodiments, the plurality of specific nucleic acids have undergone end repair prior to appending the first adaptor. In some embodiments, the end repair is blunt end repair. In some embodiments, the probe can be extended by a polymerase selected from the group consisting of a DNA polymerase, an RNA polymerase or a reverse transcriptase.

In some embodiments, prior to generating the sequencing library the plurality of probe extension products can be amplified or optionally are amplified. In some embodiments, the probe extension product can be treated with a restriction endonuclease or undergoes blunt end/end repair prior to addition of the second adaptor. In some embodiments, wherein extension of the probe extension product further comprises addition of a first adaptor. In some embodiments, amplification of the probe extension product further comprises attachment of a flow cell sequence to each end of the amplification product. In some embodiments, the restriction endonuclease treated probe extension product yields a forward read with a common end. In some embodiments, the sequence data or sequenced plurality of probe extension products can be mapped to coordinates of a genome or transcriptome to verify intended probe annealing and extension. In some embodiments, the sequence data or sequenced plurality of probe extension products can be aligned to a reference copy of a probe database to verify intended probe annealing. In some embodiments, reverse read sequences or the forward read sequences can be binned and counted according to which probe sequence they represent, wherein the number of times each probe is represented can be a measure of the number of times the starting specific nucleic acid molecule is present in the original sample. In some embodiments, the forward read comprises at least a portion of the specific nucleic acid sequence that can include at least 4, at least 5, at least 6, at least 7, at least 8, at least 9, at least 10, at least 11, at least 12, at least 13, at least 14, at least 15, at least 16, at least 17, at least 18, at least 19, at least 20, or at least 25 bases of the specific nucleic acid sequence.

In some embodiments, the first adaptor sequence or the second adaptor sequence comprises at least one of an index sequence priming site, an index nucleotide sequence, an n-random nucleotide sequence, a forward read priming site, and a reverse read priming site, and combinations thereof. In some embodiments, the second adaptor sequence or the first adaptor sequence comprises at least one of a forward read priming site, a reverse read priming site and a linker sequence, and combinations thereof. In some embodiments, the 5' first adaptor can be common to each probe extension product. In some embodiments, the 5' tail sequence can include a second adaptor sequence. In some embodiments, amplification of the probe extension product yields attachment of a flow cell sequence to each end of the amplification product.

In some embodiments, the index read comprises at least 5, at least 6, at least 7, at least 8, at least 9, at least 10, at least 11, at least 12, at least 13, at least 14, or at least 15 bases of index nucleotide sequence and the n-random base sequence. In some embodiments, the index read comprises at least 4, at least 5, at least 6, at least 7, at least 8, at least 9, or at least 10 bases of the n-random bases and the index nucleotide sequence. In some embodiments, the index read comprises at least 4, at least 5, at least 6, at least 7, at least 8, at least 9, or at least 10 bases of the n-random bases and optionally, the index nucleotide sequence. In some embodiments, the n-random base nucleotide sequence comprises at least 1, at least 2, at least 3, at least 4, at least 5, at least 6, at least 7, at least 8, at least 9, or at least 10 nucleotides. In some embodiments, the index nucleotide sequence further comprises a barcode sequence.

In some embodiments, the reverse read comprises at least one of a probe sequence and a portion of a specific nucleic acid sequence and the combination thereof. In some embodiments, the reverse read comprises at least 15, at least 20, at least 25, at least 30, at least 35, at least 40, at least 45, at least 50, at least 55, or at least 60 bases of probe sequence. In some embodiments, the reverse read comprises at least 4, at least 5, at least 6, at least 7, at least 8, at least 9, at least 10, at least 11, at least 12, at least 13, at least 14, at least 15, or at least 20 bases of specific nucleic acid sequence 3' to the probe sequence.

In a further aspect, disclosed is a composition of probe extension products produced and/or amplified by the disclosed methods.

In yet a further aspect, the plurality of nucleic acids can be derived from a sample selected from the group consisting of a tissue, an organ, a single cell, a tumor, a specimen of an organic fluid taken from a patient, freely circulating nucleic acids, a fungus, a prokaryotic organism, and a virus. In some embodiments, the patient can be known or suspected of having a tumor. In some embodiments, the organic fluid contains at least one circulating tumor cell (CTC) or a disseminated tumor cell (CTD). In some embodiments, the patient can be known or suspected of having a viral infection that can be a communicable infection or a communicable disease.

In some embodiments compositions of the present disclosure comprise a plurality of nucleic acid molecules. In some embodiments, each probe extension product is an extension product of a probe complementary to a probe target region within a specific nucleic acid molecule.

In yet a further aspect, disclosed is a kit for digital measurement of nucleic acid molecules comprising at least one or more of: an oligonucleotide adaptor; a probe complementary to a portion of a probe target region sequence; a primer complementary to said adaptor sequence; a primer complementary to a portion of the probe sequence; a ligase; a polymerase; and instructions for use of the kit. In yet a further aspect, disclosed is a kit for digital measurement of nucleic acid molecules comprising one or more aspects of the present disclosure.

In some embodiments, methods, compositions, and kits of the present disclosure comprise one or more aspects disclosed in Li et al. 2012. *Bioinformatics.* 28(10):1307-1313; Bellos et al. 2014. *Nucleic Acids Res.* 42(20):e158; Jiang et al. 2015. *Nucleic Acids Res.* 43(6):e39; Xi et al. 2011. *Proc. Natl. Acad. Sci.* 108(46):1128-1136; Fromer and Purcell. 2014. *Curr. Protoc. Hum. Genet.* 81:7.21.1-7.23.21; Sathirapongsasuti et al. 2011. *Bioinformatics.* 31(15):1-8; Krumm et al. 2012. *Genome Res.* 22(8):1525-1532; Plagnol et al. 2012. *Bioinformatics.* 28(21):2747-2754.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Pending applications U.S. Ser. No. 13/750,768, U.S. Ser. No. 14/030,761, and U.S. Ser. No. 61/903,826 are incorporated by reference in their entirety herein.

BRIEF DESCRIPTION OF THE DRAWINGS

A better understanding of the novel features and advantages of the disclosed invention can be obtained by reference to the following description that sets forth illustrative embodiments, in which the principles of the disclosed invention are utilized, and the accompanying drawings of which:

FIG. 6A—forward read, FIG. 6B—index read, FIG. 6C—reverse read.

FIG. 7 illustrates embodiments disclosed herein for identifying the regions sequenced to obtain sequence data: FIG. 7A—forward read, FIG. 7B—index read, FIG. 7C—reverse read.

FIG. 8 illustrates embodiments disclosed herein for identifying the regions sequenced to obtain sequence data: FIG. 8A—Probe containing sequence read, FIG. 8B—Specific nucleic acid sequencing read, FIG. 8C—indexing sequencing read comprising at least one of an index base read and an n-random base read or a combination thereof.

FIG. 11A shows genes in chromosome order from 1 to 6. FIG. 11B shows genes in chromosome order from 7 to 15. FIG. 11C shows genes in chromosome order from 16 to X.

FIG. 12A shows genes in chromosome order from 1 to 6. FIG. 12B shows genes in chromosome order from 7 to 14. FIG. 12C shows genes in chromosome order from 15 to X.

DETAILED DESCRIPTION

Figure 1:
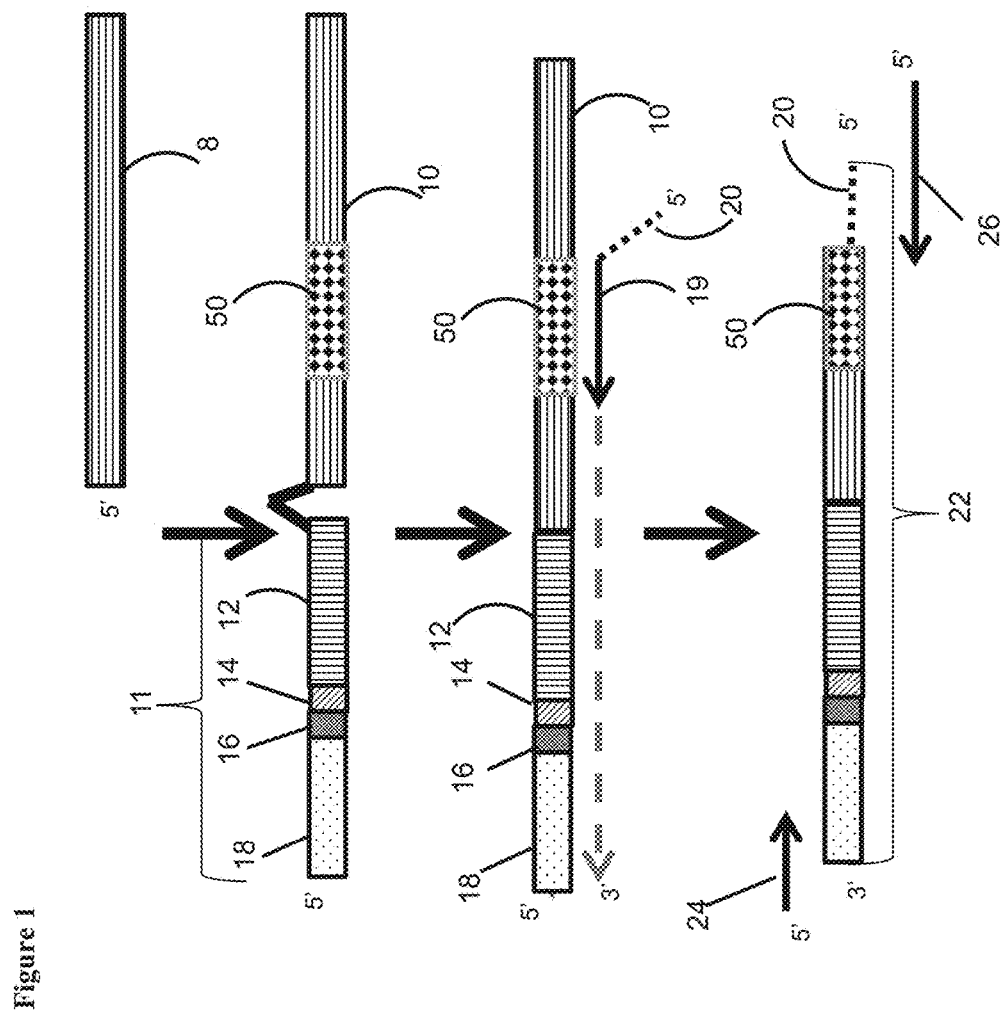
FIG. 1 is a flow chart illustrating embodiments of library generation disclosed herein using gDNA.

This disclosure describes a method for targeted nucleic acid sequencing resulting in digital measurements. Examples of where these digital measurements are useful are in digital gene expression and copy number variation. Starting material can be nucleic acid, DNA, RNA, cDNA, or double stranded cDNA. The disclosed methods, compositions and kits describe utilizing a complementary probe hybridized to its probe target region to generate probe extension products derived from the probe target region. The probe extension products are used for target enrichment and library generation proceeding high throughput sequencing.

Analysis of the sequencing data provides digital measurements of transcriptome gene expression or genomic DNA copy number variation.

Targeting probes are hybridized to a specific nucleic acid and extended with a polymerase using the target enrichment kit sold under the trademark OVATION by NuGEN. Paired end sequencing can be performed on the resulting enriched library. Reads are mapped to the genome or transcriptome and PCR duplicate reads are identified (described in patent application U.S. Ser. No. 61/903,826). Probe sequences are then counted for how many times they appear in the de-duplicated sequencing dataset as a measure of the number of copies of the original nucleic acid that were present in the starting sample. Using probe sequence counts instead of random sequence simplifies copy number analysis because precisely the same sequences are being assessed across different samples for each digital measurement. This can serve to normalize for such factors as gene length, which can change between samples due to alternative exon usage, as well as reducing known problems with sequencing read mapping to the genome or transcriptome.

The methods of the disclosed invention can be used with various applications for genetic sample analysis including but not limited to RNA-Seq analysis, digital gene expression, genotyping, copy number variation determination and whole genome amplification.

Unless otherwise specified, terms and symbols of biochemistry, nucleic acid chemistry, molecular biology and molecular genetics follow those of standard treaties and texts in the field, for example, Sambrook et al, Molecular Cloning: A Laboratory Manual, 2.sup.nd Edition (Cold Spring Harbor Laboratory, 1989); Kornberg and Baker, DNA Replication, Second Edition (W. H. Freeman, New York, 1992); Gaits, ed., Oligonucleotide Synthesis: A Practical Approach (IRL Press, Oxford, 1984); Lehninger, Biochemistry, Second Edition (Worth Publishers, New York, 1975); Eckstein, ed., Oligonucleotides and Analogs: A Practical Approach (Oxford University Press, New York, 1991); and the like.

As used herein and in the appended claims, the singular forms "a," "an," and "the" include plural referents unless the context clearly dictates otherwise. Thus, for example, reference to "a polymerase" can refer to one agent or to mixtures of such agents, and reference to "the method" includes reference to equivalent steps and/or methods known to those skilled in the art, and so forth.

Additionally, to facilitate understanding, disclosed are a number of terms as defined herein.

The term "adaptor", as used herein, can refer to an oligonucleotide of known sequence, the attachment of which to a specific nucleic acid sequence or a target polynucleotide strand of interest enables the generation of amplification-ready products of the specific nucleic acid or the target polynucleotide strand of interest. The specific nucleic acid samples can be fragmented or not prior to the addition of at least one adaptor.

Various adaptor designs are envisioned which are suitable for generation of amplification-ready products of specific sequence regions/strands of interest. For example, when double stranded adaptors are used, the two strands of the adaptor can be self-complementary, non-complementary or partially complementary. Adaptors can contain at least a partial forward sequence priming site and a random sequence.

In some embodiments, adaptors comprise an additional identifier sequence, e.g., a barcode sequence. As used herein, the term "barcode" can refer to a known nucleic acid sequence that allows some feature of a polynucleotide with which the barcode is associated to be identified. In some embodiments, the feature of the polynucleotide to be identified can be the sample from which the polynucleotide is derived. A barcode can, for example, comprise a nucleic acid sequence that when joined to a target polynucleotide can serve as an identifier of the sample from which the target polynucleotide was derived. In some embodiments, barcodes are at least 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, each barcode in a plurality of barcodes differ from every other barcode in the plurality at at least three nucleotide positions, such as at least 3, 4, 5, 6, 7, 8, 9, 10, or more positions. In some embodiments, barcodes associated with some polynucleotides are of different length than barcodes associated with other polynucleotides. Barcodes can be of sufficient length and comprise sequences that are sufficiently different to allow the identification of samples based on barcodes with which they are associated. In some embodiments, both the forward and reverse adapter can comprise at least one of a plurality of barcode sequences. In some embodiments, the first and second adaptor comprises at least one of a plurality of barcode sequences. In some embodiments, each reverse adapter comprises at least one of a plurality of barcode sequences, wherein each barcode sequence of the plurality of barcode sequences differs from every other barcode sequence in the plurality of barcode sequences. In some embodiments, both the first adapter and the second adapter comprise at least one of a plurality of barcode sequences. In some embodiments, barcodes for second adapter oligonucleotides are selected independently from barcodes for first adapter oligonucleotides. In some embodiments, first adapter oligonucleotides and second adapter oligonucleotides having barcodes are paired, such that adapters of the pair comprise the same or different one or more barcodes. In some embodiments, the methods of the invention further comprise identifying the sample from which a target polynucleotide can be derived based on the barcode sequence to which the target polynucleotide is joined. A barcode can, for example, comprise a nucleic acid sequence that when joined to a target polynucleotide serves as an identifier of the sample from which the target polynucleotide was derived.

Appending of an adaptor(s) at the desired end of the sequence region(s) of interest utilizing ligation can be suitable for carrying out the disclosed methods. Various ligation modalities are envisioned, dependent on the choice of nucleic acid, nucleic acid modifying enzymes and the resulting ligatable end of the nucleic acid. For example, when a blunt end product comprising the target region/sequence of interest can be generated, blunt end ligation can be suitable. Alternatively, where the cleavage can be carried out using a restriction enzyme of known sequence specificity, leading to the generation of cleavage sites with known sequence overhangs, suitable ends of the adaptors can be designed to enable hybridization of the adaptor to the cleavage site of the sequence region of interest and subsequent ligation. Ligation also can refer to any joining of two nucleic acid molecules that results in a single nucleic acid sequences that can be further modified to obtain the sequence of the nucleic acids in question. Reagents and methods for efficient and rapid ligation of adaptors are commercially available and are known in the art.

As used herein, the terms "amplifying", "amplification" and to "amplify" a specific nucleic acid as used herein, can refer to a procedure wherein multiple copies of the nucleic acid sample of interest are generated, for example, in the form of DNA copies. Many methods and protocols are known in the art to amplify nucleic acids, such as e.g., PCR and qPCR.

As used herein, the term "cDNA" as used herein, can refer to complementary DNA. The DNA can be synthesized in a reaction catalyzed by the enzymes reverse transcriptase and DNA polymerase from a messenger RNA (mRNA) template.

As used herein, the term "complementary" as used herein, can refer to complementarity to all or only to a portion of a sequence. The number of nucleotides in the hybridizable sequence of a specific oligonucleotide primer or probe can be such that stringency conditions used to hybridize the oligonucleotide primer or probe can prevent excessive random non-specific hybridization. The number of nucleotides in the hybridizing portion of the oligonucleotide primer or probe can be at least as great as the defined sequence on the target polynucleotide that the oligonucleotide primer or probe hybridizes to, namely, at least 5, at least 6, at least 7, at least 8, at least 9, at least 10, at least 11, at least 12, at least 13, at least 14, at least 15, at least about 20, and can be from about 6 to about 10 or 6 to about 12 of 12 to about 200 nucleotides, usually about 20 to about 50 nucleotides. The target polynucleotide/oligonucleotide can be larger than the oligonucleotide primer, primers or probe.

As used herein, the term "denaturing" as used herein, can refer to the separation of double stranded nucleic acid into single strands. Denaturation can be achieved using any of the methods known in the art including, but not limited to, physical, thermal, and/or chemical denaturation.

As used herein, the acronym "FFPE" as used herein denotes Formalin-Fixed, Paraffin Embedded. FFPE is a method used in preservation of a tissue sample in which the sample can be fixed in a formalin solution coupled with application of a wax referred to as paraffin.

As used herein, the phrase "genomic DNA" as used herein, can refer to chromosomal DNA, abbreviated as gDNA for genomic deoxyribonucleic acid. gDNA includes the genetic material of an organism.

As used herein, the term "genome" as used herein, can refer to sequences, either DNA, RNA or cDNA derived from a patient, a tissue, an organ, a single cell, a tumor, a specimen of an organic fluid taken from a patient, freely circulating nucleic acid, a fungus, a prokaryotic organism and a virus. A "transcriptome" as used herein, can be all RNA sequences that can reflect a partial or entire expressed genome of an organism.

As used herein, the term "kit" can refer to any system for delivering materials. In the context of reaction assays, such delivery systems can include elements allowing the storage, transport, or delivery of reaction components such as oligonucleotides, buffering components, additives, reaction enhancers, enzymes and the like in the appropriate containers from one location to another commonly provided with written instructions for performing the assay. Kits can include one or more enclosures or boxes containing the relevant reaction reagents and supporting materials. The kit can comprise two or more separate containers wherein each of those containers includes a portion of the total kit components. The containers can be delivered to the intended recipient together or separately.

As used herein, the phrase "nucleic acid (NA)-modifying enzyme" as used herein, can refer to a DNA-specific modifying enzyme. The NA-modifying enzyme can be selected for specificity for double-stranded DNA. The enzyme can be a duplex-specific endonuclease, a blunt-end frequent cutter restriction enzyme, or other restriction enzyme. Examples of blunt-end cutters can include Dral or Smal. The NA-modifying enzyme can be an enzyme provided by NEW ENGLAND BIOLABS. The NA-modifying enzyme can be a homing endonuclease (a homing endonuclease can be an endonuclease that does not have a stringently-defined recognition sequence). The NA-modifying enzyme can be a nicking endonuclease (a nicking endonuclease can be an endonuclease that can cleave only one strand of DNA in a double-stranded DNA substrate). The NA-modifying enzyme can be a high fidelity endonuclease (a high fidelity endonuclease can be an engineered endonuclease that has less "star activity" than the wild-type version of the endonuclease). In some embodiments, the NA-modifying enzyme can be a sequence and duplex-specific, DNA modifying enzyme.

As used herein, the phrases "nucleic acid fragment" and "specific nucleic acid" are used interchangeably and as used herein, can refer to a portion of a nucleic acid sample. The nucleic acids in the input sample can be fragmented into a population of fragmented nucleic acid molecules or to polynucleotides of one or more specific size range(s). The fragments can have an average length from about 10 to about 10,000 nucleotides, from about 50 to about 2,000 nucleotides, from about 100-2,500, 10-1,000, 10-800, 10-500, 50-500, 50-250, or 50-150 nucleotides in length. The fragments can have an average length less than 10,000 nucleotide, less than 5,000 nucleotides, less than 2,500 nucleotides, less than 2,000 nucleotides, less than 1,000 nucleotides, less than 500 nucleotides, such as less than 400 nucleotides, less than 300 nucleotides, less than 200 nucleotides, or less than 150 nucleotides.

As used herein, the phrase "specific nucleic acid sequence" or "specific sequence" as used herein, can be a polynucleotide sequence of interest, for which digital measurement and/or quantitation is desired, including but not limited to a nucleic acid fragment. The specific sequence can be known or not known, in terms of its actual sequence. A "template", as used herein, can be a polynucleotide that contains the specific nucleic acid sequence. The terms "specific sequence," "specific nucleic acid sequence," "specific nucleotide sequence," "regions of interest," or "sequence of interest" and, variations thereof, are used interchangeably.

As used herein, the phrases "qualified nucleic acid" and "qualifies the target nucleic acid fragment" as used herein, can refer to a fragment of a gDNA or RNA sequence that is: i.) an acceptable template for a DNA polymerase, i.e. the template can be free of cross-links or inhibitors to the DNA polymerase, or ii.) the template has a modification including, but not limited to, attachment at the 5' and/or 3' end a polynucleotide sequence at least one of a barcode, an adaptor, a sequence complementary to a primer and so on such that the fragment can be modified for purposes of quantitation, amplification, detection or to other methods known to one of skill in the art of gDNA and cDNA sequence analyses. The presence of inhibitors can be the result of using gDNA obtained from a tissue sample that had undergone fixation in a FFPE preparation.

As used herein, the term "oligonucleotide" can refer to a polynucleotide chain, less than 200 residues long, e.g., between 15 and 100 nucleotides long, but can also encompass longer polynucleotide chains. Oligonucleotides can be single- or double-stranded. As used in this invention, the term "oligonucleotide" can be used interchangeably with the terms "primer", "probe" and "adaptor".

"PCR" is an abbreviation of term "polymerase chain reaction," the nucleic acids amplification technology used in all methods of the present invention, and which was originally discovered and described by Mullis K. B. et al, U.S. Pat. No. 4,683,195 and Mullis K. B., U.S. Pat. No. 4,683,202. In some embodiments, PCR employs two oligonucleotide primers for each strand that are designed such as extension of one primer provides a template for another primer in the next PCR cycle. Either one of a pair of oligonucleotide primers can be named herein as a "forward" or "reverse" primer with the purpose of distinguishing the oligonucleotide primers in discussion. A PCR can consist of repetition (or cycles) of (i) a denaturation step which separates the strands of a double stranded nucleic acid, followed by (ii) an annealing step, which allows primers to anneal to positions flanking a sequence of interest; and then (iii) an extension step which extends the primers in a 5' to 3' direction thereby forming a nucleic acid fragment complementary to the target sequence. Each of the above steps can be conducted at a different temperature using an automated thermocycler. The PCR cycles can be repeated as often as desired resulting in an exponential accumulation of a target DNA fragment whose termini are usually defined by the 5' ends of the primers used. Certain exceptions to this rule can apply, including those described herein. Particular temperatures, incubation time at each step and rates of change between steps depend on many factors well-known to those of ordinary skill in the Art and the examples can be found in numerous published protocols, for example, McPherson M. J. et al. (1991 and 1995) and the like. Although conditions of PCR can vary in a broad range, a double-stranded target nucleic acid can be denatured at temperature >90° C., primers can be annealed at a temperature in the range 50-75° C., and the extension can be performed in the range 72-78° C.

The phrase "quantitative PCR" or "qPCR", as used herein, can refer to a PCR designed to measure the abundance of one or more specific target sequences in a sample. Quantitative measurements can be made using one or more reference nucleic acid sequences that can be assayed separately or together with a target nucleic acid. Techniques for quantitative PCR are well known in the art and they are exemplified in the following manuscripts that are incorporated herein by reference: Gu Z. et al (2003) J. Clin. Microbiol., 41:4636-4641; Becker-Andre M. and Hahlbrock K. (1989) Nucleic Acids Res., 17:9437-9446; Freeman W. M. et al (1999) Biotechniques, 26:112-122, 124-125; Lutfalla G. and Uze G. (2006) Methods Enzymol., 410:386-400; Clementi M. et al (1993) PCR Methods Appl. 2:191-196; Diviacco S. et al (1992) Gene, 122:313-320.

The term "portion", as used herein, can refer to less than the total length of a nucleic acid sequence, a nucleic acid sequence fragment, a specific nucleic acid sequence, a specific nucleic acid fragment, a probe, a primer and the like. A portion can be less than about 50 to about 2,000 nucleotides, from about 100-2,500, 10-1,000, 10-800, 10-500, 20-250, or 20-150 nucleotides in length.

The term "primer", as used herein, can refer to an oligonucleotide, generally with a free 3' hydroxyl group, that can be capable of hybridizing or annealing with a template (such as a specific polynucleotide, target DNA, target RNA, a primer extension product or a probe extension product) and can be also capable of promoting polymerization of a polynucleotide complementary to the template. A primer can contain a non-hybridizing sequence that constitutes a tail of the primer. A primer can still be hybridizing to a target even though its sequences are not fully complementary to the target.

The primers utilized herein can be oligonucleotides that are employed in an extension reaction by a polymerase along a polynucleotide template, such as in PCR, qPCR, an extension reaction and the like. The oligonucleotide primer can be a synthetic polynucleotide that can be single stranded, containing a sequence at its 3'-end that can be capable of hybridizing with a sequence of the target polynucleotide.

The 3' region of the primer that hybridizes with the specific nucleic acid can comprise at least 80%, preferably 90%, more preferably 95%, most preferably 100%, complementarity to a sequence or to a primer binding site.

The term, "tail sequence" can refer to a non-hybridizing sequence adjacent to and 5' of a primer or probe sequence. The term "probe extension product" can refer to a DNA fragment resulting from the hybridization of a probe and template directed synthesis initiated from the probe, e.g., within a specific nucleic acid sequence. The probe can be extended by a polymerase into an adaptor sequence, if present and appended to the specific nucleic acid. The resulting probe extension product can have both a first adaptor, e.g., the adaptor appended to the specific nucleic acid sequence and a second adaptor, e.g., found within the tail sequence of the primer or probe.

A "random primer," as used herein, can be a primer that comprises a sequence that can be designed not necessarily based on a particular or to a specific sequence in a sample, but rather can be based on a statistical expectation (or an empirical observation) that the sequence of the random primer can be hybridizable (under a given set of conditions) to one or more sequences in the sample. A random primer can be an oligonucleotide or to a population of oligonucleotides comprising a random sequence(s) in which the nucleotides at a given position on the oligonucleotide can be any of the four nucleotides, or any of a selected group of the four nucleotides (for example only three of the four nucleotides, or only two of the four nucleotides). As used herein, the notation "n-random oligonucleotide" can refer to at least zero, at least one, at least two, at least three, at least four, at least six, at least eight, at least nine, at least 10 and so on, bases within an adaptor or a priming site.

A "random nucleotide" and "n-random nucleotide sequence," as used herein, can be a nucleotide that can comprise a sequence within an adaptor or primer that can be designed not necessarily based on a particular or to a specific sequence in a sample, but rather can be based on a statistical expectation (or an empirical observation) that the adaptor or primer having the random nucleotide can be hybridizable (under a given set of conditions) to one or more sequences in a primer, an adapter or a sample. A random oligonucleotide can be an oligonucleotide or a population of oligonucleotides comprising a random sequence(s) in which the nucleotides at a given position on the oligonucleotide can be any of the four nucleotides, or any of a selected group of the four nucleotides (for example only three of the four nucleotides, or only two of the four nucleotides or only one of the nucleotides). As used herein, the notation "n-random oligonucleotide" can refer to at least zero, at least one, at least two, at least three, at least four, at least six, at least seven, at least eight, at least nine, at least 10 and so on, bases within an adaptor or a primer.

The term, "sample" as used herein, can refer to any substance containing or presumed to contain a nucleic acid of interest, and thus includes a sample of nucleic acid, cells, organisms, tissue, fluids (e.g., spinal fluid or lymph fluids), organic fluid taken from a patient, and sample including but not limited to blood, plasma, serum, urine, tears, stool, respiratory and genitourinary tracts, saliva, fragments of different organs, tissue, blood cells, circulating tumor cell (CTC) or a disseminated tumor cell (CTD), bone, samples of in vitro cell cultures or specimens that have been suspected to contain nucleic acid molecules.

The phrase, "communicable infection," and "communicable disease," can refer to infections and diseases transmittable from person to person; animal-to-animal, animal to human, or human to animal direct contact or incidental contact by virtue of proximity.

The term "PCR duplicate", as used herein, can refer to any sequencing read that is derived from the same original nucleic acid molecule and so, the same primer/probe extension product sequence, as another sequencing read and is therefore not representative of a unique nucleic acid molecule.

The term "probe", as used herein, can refer to an oligonucleotide sequence. The probe can be complementary to a probe target region. The probe sequence complementary to the probe target region can be less than about 200 residues long, between about 15 and 100 nucleotides long, but can also be intended to encompass longer polynucleotide chains. Probe target regions can be single- or double-stranded. The probe target region provides a hybridization site for a complementary probe that undergoes extension using a polymerase.

The term "probe target region", as used herein, can refer to a region within a genomic or transcriptomic database or within a genome or transcriptome sequence to which a probe has been designed. The region may extend beyond the specific complementary region and include flanking regions of the genome or transcriptome. The aligned probe sequence to its probe target region can provide verification of the specificity of probe annealing and so too the probe extension product and thus the specific nucleic acid molecule being counted.

The probe target region is within a specific nucleic acid sequence. The probe target region can be about 500 residues long and can also be between about 80 and 1000 residues. As used herein, the term "probe target region" can be used interchangeably with the term "probe hybridization site" and "probe annealing site".

The term "verified probe" or "verified probe sequence", as used herein, can refer to the sequence of the probe that has been verified to be present and hybridized to the intended specific target nucleic acid from the resulting sequencing data.

Reference will now be made in detail to exemplary embodiments of the disclosed invention. While the disclosed methods and compositions will be described in conjunction with the exemplary embodiments, it will be understood that these exemplary embodiments are not intended to limit the disclosed invention. On the contrary, the disclosed invention is intended to encompass alternatives, modifications and equivalents, which can be included in the spirit and scope of the disclosed invention.

In some embodiments, disclosed herein are methods and compositions for the quantitation of specific nucleic acid sequences of interest from a sample comprising a plurality of nucleic acids. The methods described herein can amplify specific nucleic acid sequences using a conventional adaptor, sequence specific probe target region probes, polymerase and ligation enzymes and ligation. The methods can further enable digital measurement of at least a first specific nucleic acid sequence derived from a transcriptome or genomic DNA.

Digital gene expression has been performed multiple ways, with each having significant drawbacks, thus making a new methodology important for performing proper digital counting of nucleic acid molecules. The current methods for digital nucleic acid counting can include digital PCR, high throughput sequencing and hybridization based counting as performed by the Nanostring n-counter system.

Digital PCR can be performed by diluting the starting nucleic acid material to the point of obtaining one copy per PCR vessel, either in a well in a plate or an emulsion droplet. End Point PCR can be performed for a given set of target primers and the number of wells or droplets that are positive for an amplification event can be counted. The main drawbacks to this method are the problem of obtaining exactly one copy of target nucleic acid per vessel based on the Poisson distribution, and also the reaction can be very limited to a small number of targets per nucleic acid sample that can be interrogated (low multiplex capability).

The n-counter system of Nanostring utilizes a probe hybridization scheme with single molecule resolution to count input nucleic acids by measuring fluorescent signals. The major drawbacks to this technology are the low multiplexing, due to the fluorescent tags that must be used, and the inability to target different regions on the same molecule. For example, due to the size of the fluorescent tags used, the n-counter system can be unable to interrogate the presence of two exons within the same RNA transcript.

High throughput sequencing can be considered an excellent method for digital counting of nucleic acid molecules, but it too suffers from major drawbacks. For both genomic DNA as well as RNA counting, the nucleic acids can be randomly sheared prior to sequencing. This random shearing can introduce bias into the base composition of the target, resulting in uneven amplification or sequencing of a given target of interest. The major source of ambiguity in counting nucleic acid fragments can be based on the methods currently use to count. That is, for a given gene of interest (or genomic target region), the number of sequencing reads obtained must be normalized by the size of the target region so that targets of different sizes, which would therefore necessarily generate different numbers of sequencing reads, can be compared to each other. The ambiguity occurs because the size of a target region is not necessarily fixed between samples since different length isoforms of the same gene exist at varying abundances. This can be most easily seen in the case of RNA sequencing, but applies equally to genomic DNA.

In RNA sequencing, gene counts can be expressed as RPKM or FPKM (reads/fragments per thousand million or fragments per thousand million) depending on the type of data generated. The sequencing data counts can be determined by the number of reads (or fragments in the case of paired end sequencing), the size of the target RNA (in kilobases), and the number of total sequencing reads (in millions). The problem lies in measuring the size of the target RNA; one size is assumed across all samples. However, it is well known that through alternative exon usage, the size of RNA can differ by up to many kb of sequence between different samples, thus potentially altering the size variable in the RPKM/FPKM measurement between two samples. The changes in size measurement for one gene additionally effect the RPKM/FPKM measurements for all genes in the sample as for a fixed number of sequencing reads, altering the size of one gene through alternative exon usage will change the number of reads from other genes. Just as described with RNA sequencing, genomic DNA counting can suffer from similar problems when taking into account partial duplications and deletions, which alter the size of the target region of interest between samples.

In some embodiments, disclosed herein are methods and compositions for the digital measurement of specific nucleic acid sequences from a sample having a plurality of nucleic acids. The nucleic acids can be DNA, or RNA. The nucleic acids can be single or double stranded. The DNA can be genomic DNA, cDNA, a DNA/RNA hybrid or any combination thereof. In some embodiments, the nucleic acids in an input sample can be double stranded DNA. In some embodiments, the method includes fragmenting nucleic acids in an input sample to generate nucleic acid fragments. In some embodiments, the sample is not fragmented. In some embodiments, fragmentation of the nucleic acids can be achieved through methods known in the art or described herein for fragmenting nucleic acids that can include, but are not limited to, physical (i.e. sonication), and/or enzymatic (i.e. restriction enzyme treatment) fragmentation reactions.

Physical fragmentation methods can include nebulization, sonication, and/or hydrodynamic shearing. In some embodiments, the fragmentation can be accomplished mechanically comprising subjecting the nucleic acids in the input sample to acoustic sonication. In some embodiments, the fragmentation comprises treating the nucleic acids in the input sample with one or more enzymes under conditions suitable for the one or more enzymes to generate double-stranded nucleic acid breaks. Examples of enzymes useful in the generation of nucleic acid or polynucleotide fragments can include sequence specific and non-sequence specific nucleases. Non-limiting examples of nucleases can include DNase I, Fragmentase, restriction endonucleases, variants thereof, and combinations thereof. Reagents for carrying out enzymatic fragmentation reactions are commercially available, for example as provided by NEW ENGLAND BIOLABS. For example, digestion with DNase I can induce random double-stranded breaks in DNA in the absence of Mg++ and in the presence of Mn++. In some embodiments, fragmentation comprises treating the nucleic acids in the input sample with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence.

In some embodiments, the nucleic acids in the input sample can be fragmented into a population of fragmented nucleic acid molecules or to polynucleotides of one or more specific size range(s). In some embodiments, the fragments can have an average length from about 10 to about 10,000 nucleotides. In some embodiments, the fragments can have an average length from about 50 to about 2,000 nucleotides. In some embodiments, the fragments can have an average length from about 100-2,500, 10-1,000, 10-800, 10-500, 50-500, 50-250, or 50-150 nucleotides. In some embodiments, the fragments can have an average length less than 10,000 nucleotide, such as less than 5,000 nucleotides, less than 2,500 nucleotides, less than 2,500 nucleotides, less than 1,000 nucleotides, less than 500 nucleotides, such as less than 400 nucleotides, less than 300 nucleotides, less than 200 nucleotides, or less than 150 nucleotides.

In some embodiments, fragmentation of the nucleic acids can be followed by end repair of the nucleic acid fragments. In some embodiments, non-fragmented samples can undergo end repair. End repair can include the generation of blunt ends, non-blunt ends (i.e. sticky or cohesive ends), or single base overhangs such as the addition of a single dA nucleotide to the 3'-end of the nucleic acid fragments by a polymerase lacking 3'-exonuclease activity. End repair can be performed using any number of enzymes and/or methods known in the art including, but not limited to, commercially available kits such as the ultralow next-generation sequencing library system sold under the trademark OVATION Ultralow NGS Library System by NuGEN. In some embodiments, end repair can be performed on double stranded DNA fragments to produce blunt ends wherein the double stranded DNA fragments contain 5' phosphates and 3' hydroxyls. In some embodiments, the double-stranded DNA fragments can be blunt-end polished (or "end repaired") to produce DNA fragments having blunt ends, prior to being joined to adapters. Generation of the blunt ends on the double stranded fragments can be generated by the use of a single strand specific DNA exonuclease such as for example exonuclease 1, exonuclease 7 or a combination thereof to degrade overhanging single stranded ends of the double stranded products. Alternatively, the double stranded DNA fragments can be blunt ended by the use of a single stranded specific DNA endonuclease, for example, but not limited to, mung bean endonuclease or SI endonuclease. Alternatively, the double stranded products can be blunt ended by the use of a polymerase that comprises single stranded exonuclease activity such as for example T4 DNA polymerase, or any other polymerase comprising single stranded exonuclease activity or a combination thereof to degrade the overhanging single stranded ends of the double stranded products. In some cases, the polymerase comprising single stranded exonuclease activity can be incubated in a reaction mixture that does or does not comprise one or more dNTPs. In other cases, a combination of single stranded nucleic acid specific exonucleases and one or more polymerases can be used to blunt end the double stranded fragments generated by fragmenting the sample comprising nucleic acids. In still other cases, the nucleic acid fragments can be made blunt ended by filling in the overhanging single stranded ends of the double stranded fragments. For example, the fragments can be incubated with a polymerase such as T4 DNA polymerase or Klenow polymerase or a combination thereof in the presence of one or more dNTPs to fill in the single stranded portions of the double stranded fragments. Alternatively, the double stranded DNA fragments can be made blunt by a combination of a single stranded overhang degradation reaction using exonucleases and/or polymerases, and a fill-in reaction using one or more polymerases in the presence of one or more dNTPs. Kits commercially available for blunt end repair or end polishing also include blunting kits sold under the trademark NEB and end repair kits sold under the trademark NEBNext, each sold by NEW ENGLAND BIO-LABS.

In some embodiments the fragmented specific nucleic acid can be denatured into single-stranded nucleic acid fragments. In some embodiments, the non-fragmented sample can be denatured into single-stranded nucleic acid strands. Methods for denaturing double-stranded nucleic acid into single-stranded nucleic acid are well known to one of skill in the art. Methods include but are not limited to heat denaturation, chemical denaturation and the like.

The methods described herein for quantitating specific nucleic acid fragment sequences or non-fragmented nucleic acid sample sequences can further include appending at least a first adaptor to the nucleic acid fragments or non-fragmented nucleic acid sample sequences generated by the methods described herein. In some embodiments, the at least first adaptor can be a forward adaptor. Appending the at least first adaptor to the nucleic acid fragments or non-fragmented nucleic acid sample sequences generated by methods described herein can be achieved using a ligation reaction or a priming reaction. In some embodiments, appendage of an at least first adaptor to the nucleic acid fragments or non-fragmented nucleic acid sample sequences comprises ligation. In some embodiments, ligation of the at least first adaptor to the nucleic acid fragments or non-fragmented nucleic acid sample sequences can be following end repair of the nucleic acid fragments or non-fragmented nucleic acid sample sequences. In some embodiments, the ligation of the at least first adaptor to the nucleic acid fragments or non-fragmented nucleic acid sample sequences can be following generation of the nucleic acid fragments or non-fragmented nucleic acid sample sequences without end repair of the nucleic acid fragments or non-fragmented nucleic acid sample sequences.

The at least first adaptor can be any type of adaptor known in the art including, but not limited to, conventional duplex or double stranded adaptors in which the adaptor comprises two complementary strands. In some embodiments, the first adaptor can be a double stranded DNA adaptor. In some embodiments, the first adaptor can be an oligonucleotide of known sequence and, thus, allow generation and/or use of sequence specific primers for amplification and/or sequencing of any polynucleotides to which the at least first adaptor(s) can be appended or attached. In some embodiments, the first adaptor can be a conventional duplex adaptor, wherein the first adaptor comprises sequence well known in the art. In some embodiments, the methods described herein can involve the use of a first duplex adaptor comprising double stranded DNA of known sequence that can be blunt ended and can be coupled to the double stranded nucleic acid fragments generated by the methods described herein in one orientation. In some embodiments, a first adaptor can be appended or ligated to a library of nucleic acid fragments generated by the methods described herein such that each nucleic acid fragment in the library of nucleic acid fragments or non-fragmented nucleic acid sample in the library of non-fragmented nucleic acids comprises the first adaptor ligated to one end. In some embodiments, the at least first adaptor can be appended or ligated to a single-stranded nucleic acid fragment or a non-fragmented nucleic acid sample sequences and can be incorporated into a probe extension product.

Ligation of the at least first adaptor to the nucleic acid fragments or non-fragmented nucleic acid sample sequence generates a first adaptor specific nucleic acid fragment complex or a first adaptor non-fragmented nucleic acid sample sequence, a ligation product. In some embodiments, the first adaptor specific nucleic acid fragment complex can be denatured. In some embodiments, a first adaptor non-fragmented nucleic acid sample sequence can be denatured. Denaturation can be achieved using any of the methods known in the art including, but not limited to, physical, thermal, and/or chemical denaturation. In some embodiments, denaturation can be achieved using thermal or heat denaturation. In some embodiments, denaturation of the at least first adaptor specific nucleic acid fragment complex or the at least first adaptor non-fragmented nucleic acid sample sequence generates single stranded nucleic acid fragments or non-fragmented nucleic acid sample sequence comprising the at least first adaptor sequence at only the 5' end of the nucleic acid fragments or non-fragmented nucleic acid sample sequence as depicted, for example, in FIG. 1.

In some embodiments, the nucleic acid fragments or non-fragmented nucleic acid sample sequences comprising first adaptor sequence appended to either the 5' end or both the 5' and 3' end can be denatured to generate single stranded nucleic acid fragments or non-fragmented nucleic acid sample sequence comprising first adaptor sequence appended to either the 5' end or both the 5' and 3' end. In some embodiments, the methods of the present invention described herein can be used to generate a plurality of single stranded nucleic acid fragments or non-fragmented nucleic acid sample sequence comprising first adaptor sequence appended to either the 5' end or both the 5' and 3' end. In some embodiments, an oligonucleotide probe comprising at a first end sequence complementary to a probe target region sequence of interest present in a single stranded specific nucleic acid and at a second end sequence from a second adaptor, wherein the second adaptor sequence is not complementary to the probe target region can be annealed to the single stranded specific nucleic acid fragments or non-fragmented nucleic acid sample sequence. In some embodiments, the second adaptor sequence can be sequence from a reverse adaptor.

In some embodiments, the probe target region sequence of interest can be present in one or more of the single stranded specific nucleic acid fragments or non-fragmented nucleic acid sample sequences. In some embodiments, different or distinct probe target region sequences of interest can be present in one or more of the single stranded nucleic acid fragments or non-fragmented nucleic acid sample sequences. In some embodiments, one or more oligonucleotides can comprise sequence complementary to the same sequence of interest present in one or more single stranded nucleic acid fragments or non-fragmented nucleic acid sample sequences. In this embodiment, the one or more oligonucleotides can comprise sequence that can be complementary to different parts or to regions of the same sequence of interest. In some embodiments, the different regions can be adjacent to each other. In some embodiments, the different regions can be non-adjacent to each other. In some embodiments, the one or more oligonucleotides that comprise sequence complementary to the same target nucleic acid sequence of interest can further comprise the same second adaptor sequence. In some embodiments, one or more probe oligonucleotides can comprise sequence complementary to different or to distinct sequences of interest that can be present in one or more single stranded nucleic acid fragments or non-fragmented nucleic acid sample sequence. In some embodiments, the one or more oligonucleotide probes that comprise sequence complementary to different or to distinct target nucleic acid sequences of interest and can further comprise the same second adaptor sequence. In some embodiments, the sequence complementary to the target sequence of interest can be at the 3' end of the oligonucleotide probe and the second adaptor sequence can be at the 5' end of the oligonucleotide. In some embodiments, the second adaptor sequence can be non-complementary to the target nucleic acid sequence of interest. In this manner, the second adaptor sequence serves as a tail. The second adaptor sequence can be a conventional adaptor sequence. In some embodiments, the second adaptor sequence can be a conventional adaptor sequence that can be different than or distinct from the sequence of the first adaptor appended to the single stranded nucleic acid fragment or non-fragmented nucleic acid sample sequence as described above. In some embodiments, the second adaptor sequence can be of known sequence and, thus, allow generation and/or use of sequence specific primers for amplification and/or sequencing of any polynucleotides to which the second adaptor sequence can be appended or attached. In a separate embodiment, the oligonucleotide probe can be annealed to the specific nucleic acid fragments or non-fragmented nucleic acid sample sequences comprising the first adaptor sequence appended to either the 5' end or both the 5' and 3' end without prior denaturation. In this embodiment, annealing of the oligonucleotide can be via formation of a triple helix or triplex between the oligonucleotide and a double stranded nucleic acid fragment or non-fragmented nucleic acid sample sequence comprising the first adaptor sequence appended to either the 5' end or both the 5' and 3' ends of the double stranded nucleic acid fragment or non-fragmented nucleic acid sample sequence. In this embodiment, the double stranded nucleic acid fragment or non-fragmented nucleic acid sample sequence comprises a sequence of interest and can be present amongst a plurality of double stranded nucleic acid fragments or non-fragmented nucleic acid sample sequence comprising first adaptor sequence appended to either the 5' end or both the 5' and 3' end. Further to this embodiment, the oligonucleotide probe comprises sequence complementary to the probe target region in the double stranded specific nucleic acid fragment or non-fragmented nucleic acid sample sequence. Overall, the use of the oligonucleotide probe comprising sequence complementary to a probe target region sequence of interest present in a nucleic acid fragment or non-fragmented nucleic acid sample sequence amongst one or more or a plurality of specific nucleic acid fragments or non-fragmented nucleic acid sample sequences allows for selective binding and subsequent enrichment of said nucleic fragment or non-fragmented nucleic acid sample sequence using the methods described herein.

Following annealing of the oligonucleotide probe as described above, a polymerase can be used to extend the oligonucleotide probe. In some embodiments, the polymerase can be a DNA dependent DNA polymerase. In some embodiments, the DNA dependent DNA polymerase can be any of the DNA dependent DNA polymerases as described herein and extension of the oligonucleotide can be by any of the methods known in the art. In some embodiments, an oligonucleotide probe comprising the second adaptor sequence, wherein the second adaptor sequence is not complementary to the probe target region nucleic acid, and sequence complementary to a probe target region sequence of interest present in a specific nucleic acid fragment comprising a first adaptor appended to one and/or both ends can be annealed to the nucleic acid fragment and extended with a polymerase to generate an probe extension product comprising the first adaptor sequence at a first end and the second adaptor sequence at a second end. In some embodiments, the specific nucleic acid fragment can be present amongst a plurality of nucleic acid fragments comprising first adaptor appended to one and/or both ends. In this embodiment, the probe extension product can only be generated for a nucleic acid fragment that contains the probe target region sequence of interest.

In some embodiments, the probe extension product generated by the methods described herein can be subjected to an amplification reaction. In some embodiments, the amplification reaction can be exponential, and can be carried out at various temperature cycles. The amplification reaction can be an isothermal reaction. In some embodiments, the amplification can be a quantitative polymerase chain reaction (qPCR). In some embodiments, the amplification reaction can be isothermal. In some embodiments, the probe extension product comprises at least first adaptor sequence on one end and a second adaptor sequence on the other end as generated by the methods described herein. In some embodiments, the probe extension product can be amplified using a first primer comprising sequence complementary to the first adaptor and a second primer having sequence complementary to a 5' tail sequence, in the strand complementary to the probe target region within the specific nucleic acid strand. In this manner probe extension products comprising both the first adaptor sequence and a probe target region can be amplified and so enriched. Probe extension products having both the at least first adaptor sequence and a probe target region sequence are amplified, wherein an amplified probe extension product generated from said ligated specific nucleic acid fragment or non-fragmented nucleic acid sample sequence can be quantitated. In some embodiments, the at least first adaptor sequence and/or the second adaptor sequence can comprise an identifier sequence. In some embodiments, the identifier sequence can be a barcode sequence. In some embodiments, the barcode sequence can be unique for the at least first adaptor. In some embodiments, the at least first adaptor and/or the second adaptor sequence can comprise sequence that can be used for downstream applications such as, for example, but not limited to, sequencing and specific nucleic acid identification after a sequencing reaction. In some embodiments, the at least first adaptor and/or the second adaptor sequence can comprise flow cell sequences 33 and 35 (FIG. 5) that can be used for sequencing with the sequencing method developed by Illumina and described herein.

Figure 2:
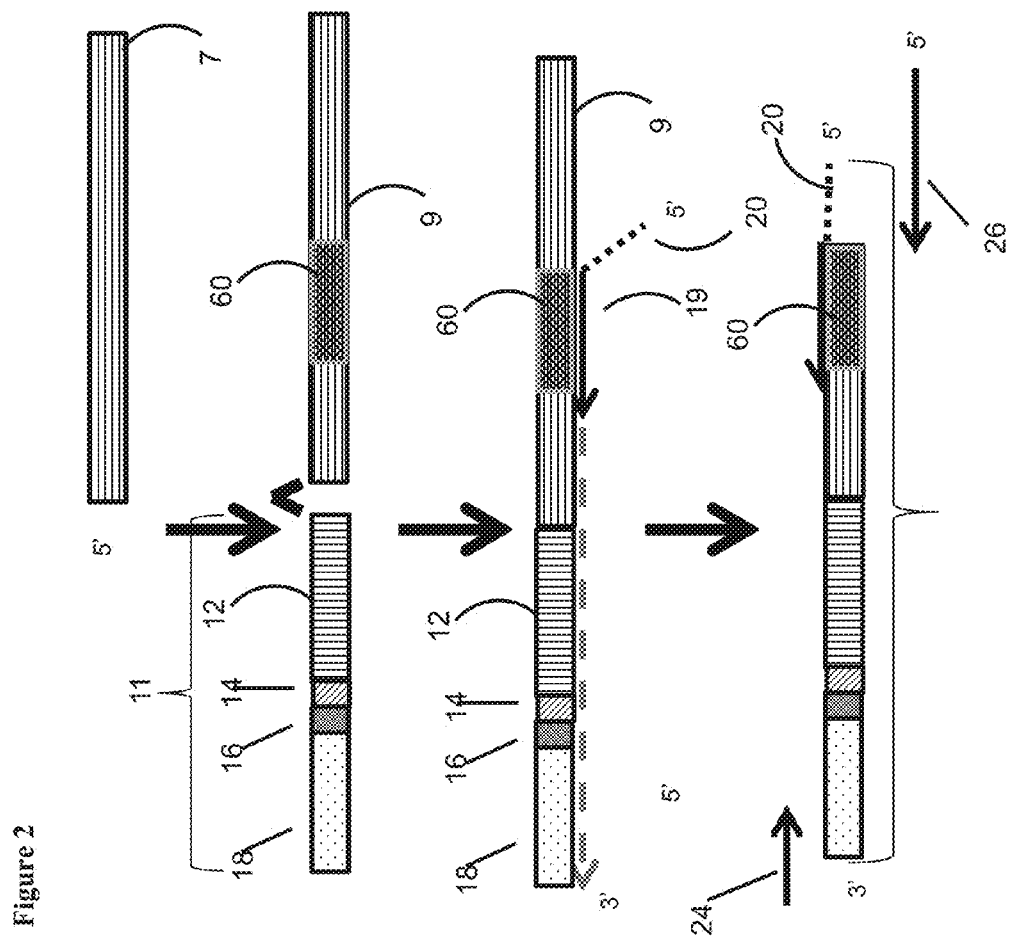
FIG. 2 is a flow chart illustrating embodiments of library generation disclosed herein using cDNA.

A schematic of a disclosed embodiment of the methods described herein for quantitating specific nucleic acid sequence fragments of interest is illustrated in FIG. 1 and FIG. 2. The numbering scheme used in the figures is illustrative only. The same number appearing in more than one figure is not intended to indicate an identical oligonucleotide sequence, in whole or in part but rather a component, site or region of reference for practicing the disclosed methods.

The methods of FIG. 1 and FIG. 2 illustrate generation of a ligated library of nucleic acid fragments, non-fragmented nucleic acid samples or inserts wherein each nucleic acid sequence of the ligated library comprises a common forward read priming site within the adaptor and a specific probe target region sequence such that PCR amplification using a primer complementary to the forward read priming site and a primer complementary to the reverse read priming site within the probe extension product comprising the probe target region provides sequencing coverage to allow quantitation of the specific nucleic acid molecule having the specific probe target region sequence.

FIG. 1 illustrates the use of sheared gDNA. Sheared DNA 8 has adaptor 11 ligated to the 5' end of gDNA having specific nucleic acid fragment 10. The fragment 10 includes probe target region 50. The adaptor can comprise at least one of a sequencing read 1 forward oligonucleotide priming site 12, a n-random oligonucleotide base(s) such as a 6N oligonucleotide sequence 14, an index base oligonucleotide sequence 16, and depending on the high throughput sequencing method used, an index priming site 18. Upon ligation of the adaptor 11 the specific nucleic acid fragment 10 can have a unique identifier sequence label, the index read plus the n-random oligonucleotide. The index sequence 16 is used to identify the specific nucleic acid sample and the 6N oligonucleotide sequence 14 is used in marking duplicate sequencing reads. Probe oligonucleotide sequence 19 having a 5' tail oligonucleotide sequence 20 can be complementary to and hybridize to probe target region 50 and can be extended in a single primer extension reaction in the presences of dNTPs and DNA polymerase through the adaptor 11. The resulting probe extension product 22 can be amplified using forward primer 24 that can be partially complementary to index priming site 18 and reverse primer 26 that can be partially complementary to the reverse complement of the 5' tail sequence 20. The amplification reaction enriches the presence of specific nucleic acid 10 having probe target region 50 to generate a library of specific nucleic acid sequences.

As illustrated in FIG. 2 a similar single primer extension reaction can be applicable to cDNA. cDNA 7 has adaptor 11 ligated to the 5' end of specific nucleic acid fragment 9. The fragment 9 includes probe target region 60. The adaptor can comprise at least one of a forward sequencing read oligonucleotide priming site 12, a known random oligonucleotide base(s) such as a 6N oligonucleotide sequence 14, an index base oligonucleotide sequence 16, and depending on the high throughput sequencing method used, an index sequencing read priming site 18. The index sequence 16 is used to identify the specific nucleic acid sample and the 6N oligonucleotide sequence 14 is used in identifying duplicate sequencing reads. Probe oligonucleotide sequence 19 having a 5' tail oligonucleotide sequence 20 can be complementary to and hybridizes to probe target region sequence 60 and can be extended in a single primer extension reaction in the presences of dNTPs and DNA polymerase through the adaptor 15. The resulting probe extension product 21 can be amplified using forward primer 24 that can be partially complementary to 18 and reverse primer 26 that can be partially complementary to the reverse complement of the 5' tail sequence 20. The amplification reaction enriches the presence of specific nucleic acid 9 having probe target region 60 to generate a library of specific nucleic acid sequences.

Figure 3:
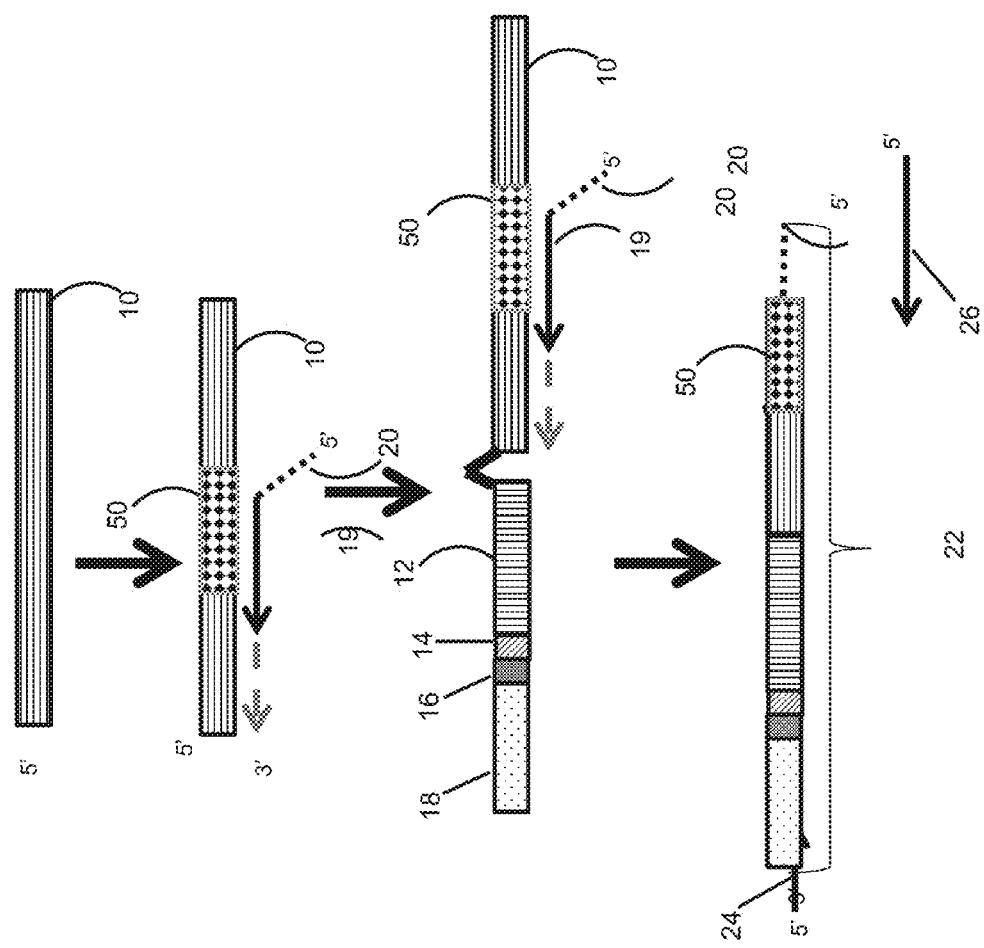
FIG. 3 is a flow chart illustrating embodiments of library generation disclosed herein using double-stranded gDNA.
Figure 4:
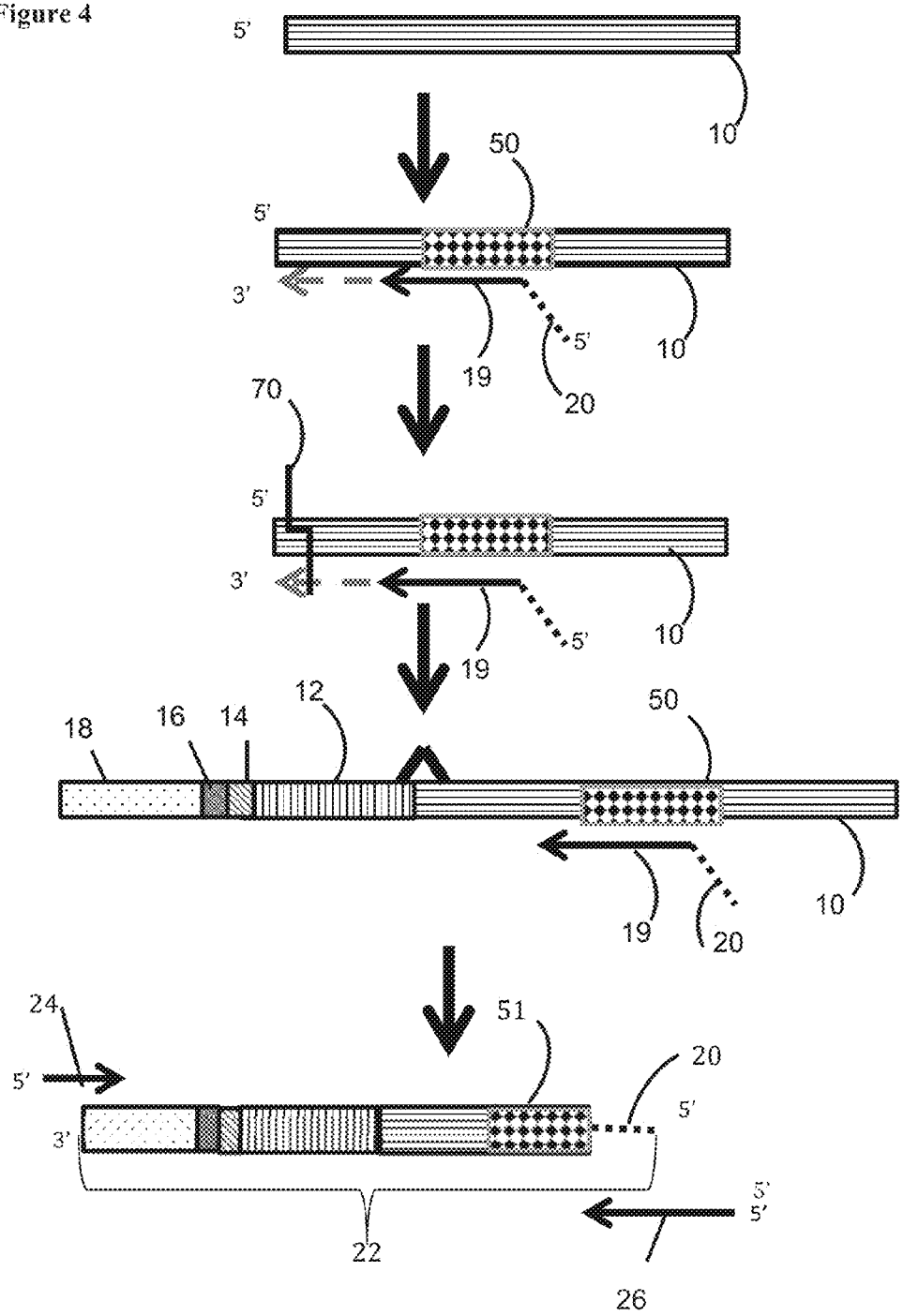
FIG. 4 is a flow chart illustrating embodiments of library generation disclosed herein using double-stranded gDNA.

A schematic of a disclosed embodiment of the methods described herein for quantitating specific nucleic acid sequence fragments of interest is illustrated in FIG. 3 and FIG. 4 for double stranded gDNA. The numbering scheme used in the figures is illustrative only. The same number appearing in more than one figure is not intended to indicate an identical oligonucleotide sequence, in whole or in part but rather a component, site or region of reference for practicing the disclosed methods.

The methods of FIG. 3 and FIG. 4 illustrate generation of a sequencing library of nucleic acid fragments, non-fragmented nucleic acid samples or inserts wherein each nucleic acid sequence of the sequencing library comprises a common forward priming site within one adaptor and a specific probe target region sequence such that there can be sequencing coverage to allow quantitation of the specific nucleic acid molecule having the specific probe target region sequence. The sequencing can be done using a sequencing library made from the ligated probe extension products with or without PCR amplification using a primer complementary to the common forward priming site and a primer complementary to the specific probe target region sequence within the specific nucleic acid sequence.

FIG. 3 illustrates the use of sheared gDNA. Sheared gDNA having specific nucleic acid 10 includes probe target region 50. Probe oligonucleotide sequence 19, having a 5' tail oligonucleotide sequence 20, can be complementary to and hybridizes to probe target region sequence 50 and can be extended in a single probe extension reaction in the presences of dNTPs and DNA polymerase through the end of specific nucleic acid 10 creating double-stranded DNA. The resulting probe extension product can have an adaptor ligated to the 3' end of specific nucleic acid fragment 10. The adaptor can comprise at least one of a forward sequencing read 1 oligonucleotide priming site 12, a n-random oligonucleotide base(s) such as a 6N oligonucleotide sequence 14, an index base oligonucleotide sequence 16, and depending on the high throughput sequencing method used, an index priming site 18. The index sequence 16 is used to identify the specific nucleic acid sample and the 6N oligonucleotide sequence 14 is used in marking duplicate sequencing reads. The ligated product 22 can be amplified using forward primer 24 that can be partially complementary to index priming site 18 and reverse primer 26 that can be partially complementary to the reverse complement of 5' tail sequence 21. The amplification reaction can enrich for the presence of specific nucleic acid 10 having probe target region 50 to generate a library of specific nucleic acid sequences.

FIG. 4 illustrates the use of sheared gDNA. Sheared gDNA having specific nucleic acid 10 includes probe target region 50. Probe oligonucleotide sequence 19, having a 5' tail oligonucleotide sequence 20, can be complementary to and hybridizes to probe target region sequence 50 and can be extended in a single probe extension reaction in the presences of dNTPs and DNA polymerase through the end of gDNA 10 creating double-stranded DNA. The resulting probe extension product can be digested by a restriction enzyme 70. Exemplary restriction enzymes include but are not limited to XbaI, EcoRI, EcoRV, and BamHI. Following restriction enzyme digestion an adaptor can be ligated to the end of double-stranded gDNA having specific nucleic acid fragment 10. The adaptor can comprise at least one of a Read 1 forward oligonucleotide priming site 12, a n-random oligonucleotide base(s) such as a 6N oligonucleotide sequence 14, an index base oligonucleotide sequence 16, and depending on the high throughput sequencing method used, an index priming site 18. The index sequence 16 is used to identify the specific nucleic acid sample and the 6N oligonucleotide sequence 14 is used in marking duplicate sequencing reads. The ligated product 22 can be amplified using forward primer 24 that can be partially complementary to index priming site 18 and reverse primer 26 that can be partially complementary to 5' tail sequence 21 as illustrated in FIG. 3. The amplification reaction can enrich for the presence of specific nucleic acid 10 having probe target region 50 to generate a library of specific nucleic acid sequences.

Figure 5:
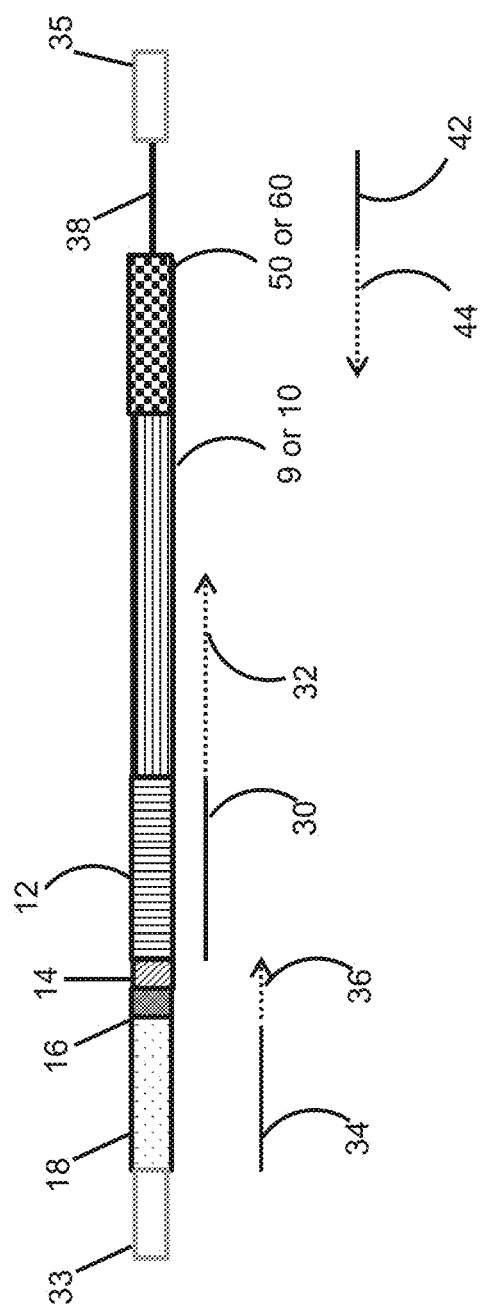
FIG. 5 illustrates embodiments disclosed herein for constructing a sequencing library and regions of sequencing reads.

As illustrated in FIG. 5 (numbering refers the numbering used in FIG. 1 or FIG. 2) a similar single primer extension reaction can be applicable to either gDNA or cDNA to create a sequencing library for a variety of sequencing platforms. The gDNA or cDNA (sheared or not) 10 or 9 has adaptor 11 ligated to the 5' end of specific nucleic acid fragment 10 or 9. The fragment 10 or 9 includes probe target region 50 or 60, respectively. The adaptor can comprise at least one of a forward oligonucleotide priming site 12, a known random oligonucleotide base(s) such as a 6N oligonucleotide sequence 14, an index base oligonucleotide sequence 16, and depending on the high throughput sequencing method used, an index priming site 18. Probe oligonucleotide sequence 19 having a 5' tail oligonucleotide sequence 20 and can be complementary to and hybridizes to probe target region sequence 50 or 60 and can be extended in a single primer extension reaction in the presences of dNTPs and DNA polymerase through the adaptor 11. The resulting probe extension product 21 or 22 can be amplified using forward primer 24 that can be partially complementary to 18 and reverse primer 26 that can be partially complementary to 5' tail sequence 20. The amplification reaction enriches the presence of specific nucleic acid 10 or 9 having probe target region 50 or 60 to generate a library of specific nucleic acid sequences.

Libraries can be prepared using the target enrichment systems sold under the trademark OVATION by NuGEN by selectively amplifying by PCR those probe extension product sequences having the selected probe target region sequence of interest. FIG. 5 illustrates an example of a nucleic acid library used in high throughput sequencing when using the Illumina high throughput sequencing platform. Specific sequence read regions of each sequence library can be analyzed for digital measurement of e.g. gene expression or copy number variation quantitation.

In some embodiments, the specific nucleic acids can be tagged with an indicator molecule, including but not limited to, biotin. The tagged specific nucleic acid molecules can then be distinguished as originating from original sample molecules. In some embodiments, attachment of an indicator molecule can be accomplished via ligation or polymerase addition of a labeled nucleotide, e.g., a biotinylated nucleotide. Probes that can be complementary to a probe target region can then be hybridized to the tagged nucleic acids with or without probe extension by polymerase. In some embodiments, non-hybridizing probes are removed, for example, by capturing the tagged nucleic acids via a biotin/streptavidin interaction. In some embodiments, probes that hybridized to the targets are captured along with the targets. Following removal of non-hybridizes probes, the captured probes are eluted off of the target nucleic acids and counted. In some embodiments, counting can be done by sequencing via the Illumina platform and counting those tags. In some embodiments, the probe can be tagged with a nanopore or fluorescent tagging as is known to one of skill in the art.

Input Nucleic Acid

The input can be a human nucleic acid. In some embodiments, the input can be DNA. In some embodiments, the input human nucleic acid can be complex DNA, such as double-stranded DNA, genomic DNA or mixed DNA from more than one organism. In some embodiments, the input can be RNA. In some embodiments, the RNA can be obtained and purified using standard techniques in the art and can include RNAs in purified or unpurified form, which can include, but are not limited to, mRNAs, tRNAs, snRNAs, rRNAs, small non-coding RNAs, microRNAs, polysomal RNAs, pre-mRNAs, intronic RNA, cell free RNA and fragments thereof. The non-coding RNA, or ncRNA can include snoRNAs, microRNAs, siRNAs, piRNAs and long ncRNAs. In some embodiments, the DNA fragments can be derived from RNA that has been converted to cDNA through a first strand synthesis reaction using any of the methods well known in the art for generating cDNA from an RNA template which can include, but is not limited to, combining the RNA with a primer (i.e. random primer), and reverse transcribing the RNA template with an RNA-dependent DNA polymerase. In some embodiments, the DNA fragments can be derived from RNA that has been converted to double stranded cDNA through a first and second strand synthesis reaction using any of the methods well known in the art.

In some embodiments, the input DNA can be cDNA made from a mixture of genomes of different species. The input complex also can be from a mixture of genomes of different humans. The input DNA can be cDNA made from a mixture of genomes of different humans. The input DNA can be of a specific species, for example, human, rat, mouse, other animals, specific plants, bacteria, algae, viruses, and the like.

The input complex also can be from a mixture of genomes of different species such as host-pathogen, bacterial populations and the like. Alternatively, the input nucleic acid can be from a synthetic source. The input DNA can be mitochondrial DNA. The input DNA can be cell-free DNA. The cell-free DNA can be obtained from, e.g., a serum or plasma sample. The input DNA can comprise one or more chromosomes. For example, in cases wherein the input DNA can be from a human, the DNA can comprise one or more of chromosome 1, 2, 3, 4, 5, 6, 7, 8, 9, 10, 11, 12, 13, 14, 15, 16, 17, 18, 19, 20, 21, 22, X, or Y. The DNA can be from a linear or circular genome. The DNA can be plasmid DNA, cosmid DNA, bacterial artificial chromosome (BAG), or yeast artificial chromosome (YAC). The input DNA can be from more than one individual human. The input DNA can be double stranded or single stranded. The input DNA can be part of chromatin. The input DNA can be associated with histones.

In some embodiments, the probe oligonucleotide can be directed to a specific nucleic acid sequence of interest and can be designed to hybridize to single-stranded specific nucleic acid targets having a probe target region within the specific nucleic acid. In some embodiments, the probes targeting the selected sequence regions of interest can be designed to hybridize to single-stranded DNA or cDNA probe target regions. In the case where the input nucleic acid sample comprises genomic DNA or other double-stranded DNA, the input nucleic acid sample can be first denatured to render the target single stranded and enable hybridization of the oligonucleotide probes to the desired probe target region sequence regions of interest. In some embodiments, the other double-stranded DNA can be double-stranded cDNA generated by first and second strand synthesis of one or more target RNAs. In these embodiments, the methods and compositions described herein can allow for region-specific enrichment and amplification of a plurality of specific nucleic acid sequence regions of interest containing a plurality of probe target regions. In some embodiments, the methods and compositions described herein allow for multiplex amplification, enrichment and quantitation of at least two or more distinct specific nucleic acid sequence fragments or non-fragmented nucleic acid sample sequences, each having a distinct region of interest containing a corresponding distinct probe target region.

In other embodiments, the probes targeting the selected sequence regions of interest can be designed to hybridize to double-stranded nucleic acid target fragments or non-fragmented nucleic acid sample sequences, without denaturation of the double stranded nucleic acids fragment or non-fragmented nucleic acid sample sequence. In other embodiments, the probes targeting the selected sequence regions of interest can be designed to hybridize to a double-stranded DNA target, without denaturation of the dsDNA. In these embodiments, the probes targeting the selected sequence regions of interest can be designed to form a triple helix (triplex) at the selected sequence regions of interest. The hybridization of the probes to the double-stranded DNA sequence regions of interest can be carried out without prior denaturation of the double stranded nucleic acid sample. In such embodiments, the methods and compositions described herein can allow for region-specific quantitation as well as strand-specific amplification and quantitation of sequence regions of interest. This method can be useful for generation of copies of strand specific sequence regions of interest from complex nucleic acid without the need to denature the dsDNA input DNA, thus enabling quantitation and analysis of multiplicity of sequence regions of interest in the native complex nucleic acid sample. The method can find use for studies and analyses carried out in situ, enable studies and analysis of complex genomic DNA in single cells or collection of very small well-defined cell population, as well as permit the analysis of complex genomic DNA without disruption of chromatin structures.

In some embodiments, disclosed herein are adaptors comprising an additional identifier sequence, e.g. a barcode sequence. In some embodiments, the at least first adaptor comprises at least one of a plurality of barcode sequences. In some embodiments, each reverse adapter comprises at least one of a plurality of barcode sequences, wherein each barcode sequence of the plurality of barcode sequences differs from every other barcode sequence in the plurality of barcode sequences. In some embodiments, barcodes for second adapter oligonucleotides can be selected independently from barcodes for at least first adapter oligonucleotides. In some embodiments, first adapter oligonucleotides and second adapter oligonucleotides having barcodes can be paired, such that adapters of the pair comprise the same or different one or more barcodes. In some embodiments, the methods of the invention can further comprise identifying the sample from which a target polynucleotide is derived based on the barcode sequence to which the target polynucleotide is joined. A barcode can, for example, comprise a nucleic acid sequence that when joined to a target polynucleotide serves as an identifier of the sample from which the target polynucleotide was derived.

Various adaptor designs can be envisioned which can be suitable for generation of amplification-ready products of probe target region sequence regions/strands of interest. In some embodiments the at least first adaptor can be single or double stranded. For example, when double stranded the two strands of the adaptor can be self-complementary, non-complementary or partially complementary. Recently, many improvements have been made in adaptor design that has reduced the occurrence of adapter dimer. These improvements can include the use of nucleotide analogs and structured oligonucleotides, and have allowed for use of higher concentrations of oligonucleotides in ligation reactions. The higher concentrations of adapters in ligation reactions have enabled researchers to produce high quality libraries from as few as 150 copies of genome. Ligation of adaptors to the ends of DNA fragments, in particular those fragments containing the regions of interest can be suitable for carrying out the methods of the invention. Various ligation modalities can be envisioned, dependent on the choice of nucleic acid modifying enzymes and the resulting double-stranded DNA cleavage. For example, when a blunt end product comprising the target region/sequence of interest is generated, blunt end ligation can be suitable. Alternatively, where the cleavage can be carried out using a restriction enzyme of known sequence specificity, leading to the generation of cleavage sites with known sequence overhangs, suitable ends of the adaptors can be designed to enable hybridization of the adaptor to the cleavage site of the sequence region of interest and subsequent ligation. Reagents and methods for efficient and rapid ligation of adaptors are commercially available and are known in the art.

Nucleic Acid Modifying Enzymes

The nucleic acid (NA)-modifying enzyme can be DNA-specific modifying enzyme. The NA-modifying enzyme can be selected for specificity for double-stranded DNA. The enzyme can be a duplex-specific endonuclease, a blunt-end frequent cutter restriction enzyme, or other restriction enzyme. Examples of blunt-end cutters can include DraI or SmaI. The NA-modifying enzyme can be an enzyme provided by NEW ENGLAND BIOLABS. The NA-modifying enzyme can be a homing endonuclease (a homing endonuclease can be an endonuclease that does not have a stringently-defined recognition sequence). The NA-modifying enzyme can be a nicking endonuclease (a nicking endonuclease can be an endonuclease that can cleave only one strand of DNA in a double-stranded DNA substrate). The NA-modifying enzyme can be a high fidelity endonuclease (a high fidelity endonuclease can be an engineered endonuclease that has less "star activity" than the wild-type version of the endonuclease).

DNA-Dependent DNA Polymerases

DNA-dependent DNA polymerases for use in the methods and compositions of the invention can be capable of effecting extension of a probe target region or primer according to the methods of the invention. In some embodiments, a DNA-dependent DNA polymerase can be one that is capable of extending a probe target region, a nucleic acid primer and the like in the presence of the DNA and/or cDNA template. Exemplary DNA dependent DNA polymerases suitable for the methods of the present invention include but are not limited to Klenow polymerase, with or without 3'-exonuclease, Bst DNA polymerase, Bsu polymerase, phi29 DNA polymerase, Vent polymerase, Deep Vent polymerase, Taq polymerase, T4 polymerase, and E. coli DNA polymerase 1, derivatives thereof, or to a mixture of polymerases. In some cases, the polymerase does not comprise a 5'-exonuclease activity. In other cases, the polymerase comprises 5' exonuclease activity. In some cases, the primer or oligonucleotide extension product of the present invention can be performed using a polymerase comprising strong strand displacement activity such as for example Bst polymerase. In other cases, the primer extension of the present invention can be performed using a polymerase comprising weak or no strand displacement activity. One skilled in the art can recognize the advantages and disadvantages of the use of strand displacement activity during the primer extension step, and which polymerases can be expected to provide strand displacement activity, see for example, Polymerases by NEW ENGLAND BIOLABS.

Methods of Amplification

The methods, compositions and kits described herein can be useful to generate amplification-ready products for downstream applications such as massively parallel sequencing (i.e. next generation sequencing methods), generation of libraries with enriched population of sequence regions of interest, or hybridization platforms. Methods of amplification are well known in the art. Suitable amplification reactions can be exponential or isothermal and can include any DNA amplification reaction, including but not limited to polymerase chain reaction (PCR), strand displacement amplification (SDA), linear amplification, multiple displacement amplification (MDA), rolling circle amplification (RCA), single primer isothermal amplification (SPIA, see e.g. U.S. Pat. No. 6,251,639), Ribo-SPIA, or a combination thereof. In some cases, the amplification methods for providing the template nucleic acid can be performed under limiting conditions such that only a few rounds of amplification (e.g., 1, 2, 3, 4, 5, 6, 7, 8, 9, 10, 11, 12, 13, 14, 15, 16, 17, 18, 19, 20,21,22, 23,24, 25,26, 27, 28, 29, 30 etc.), such as for example as can be commonly done for cDNA generation. The number of rounds of amplification can be about 1-30, 1-20, 1-15, 1-10, 5-30, 10-30, 15-30, 20-30, 10-30, 15-30, 20-30, or 25-30.

PCR is an in vitro amplification procedure based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, can be positioned so that the polymerase catalyzed extension product of one primer can serve as a template strand for the other, leading to the accumulation of a discrete double stranded fragment whose length can be defined by the distance between the 5' ends of the oligonucleotide primers. Additional amplification methods are further described in U.S. Ser. No. 13/750,768 filed Jan. 25, 2013, incorporated by reference herein in its entirety.

In some embodiments, the amplification can be exponential, e.g. in the enzymatic amplification of specific double stranded sequences of DNA by a polymerase chain reaction (PCR). In other embodiments the amplification method can be linear. In other embodiments the amplification method can be isothermal.

Downstream Applications

One aspect of the invention is that the methods and compositions disclosed herein can be efficiently and cost-effectively utilized for downstream analyses, such as next generation sequencing or hybridization platforms, with minimal loss of biological material of interest. The methods disclosed herein can also be used in the analysis of genetic information of selective genomic regions of interest (e.g., analysis of SNPs, copy number variation, or other disease markers) as well as digital gene expression from transcriptome analyses and genomic regions that can interact with the selective region of interest.

Sequencing

For example, the methods of the invention can be useful for sequencing by the method commercialized by Illumina, as described U.S. Pat. Nos. 5,750,341; 6,306,597; and 5,969,119. In general, double stranded fragment polynucleotides can be prepared by the methods of the present invention to produce amplified nucleic acid sequences tagged at one (e.g., (A)/(A') or both ends (e.g., (A)/(A') and (C)/(C')). In some cases, single stranded nucleic acid tagged at one or both ends can be amplified by the methods of the present invention (e.g., by SPIA or linear PCR). The resulting nucleic acid can then be denatured and the single-stranded amplified polynucleotides can be randomly attached to the inside surface of flow-cell channels. Unlabeled nucleotides can be added to initiate solid-phase bridge amplification to produce dense clusters of double-stranded DNA. To initiate the first base sequencing cycle, four labeled reversible terminators, primers, and DNA polymerase can be added. After laser excitation, fluorescence from each cluster on the flow cell can be imaged. The identity of the first base for each cluster can then be recorded. Cycles of sequencing can be performed to determine the fragment sequence one base at a time.

In some embodiments, the methods of the invention can be useful for preparing target polynucleotides for sequencing by the sequencing by ligation methods commercialized by Applied Biosystems (e.g., SOLiD sequencing). In other embodiments, the methods can be useful for preparing target polynucleotides for sequencing by synthesis using the methods commercialized by 454/Roche Life Sciences, including but not limited to the methods and apparatus described in Margulies et al., Nature (2005) 437:376-380 (2005); and U.S. Pat. Nos. 7,244,559; 7,335,762; 7,211,390; 7,244,567; 7,264,929; and 7,323,305. In other embodiments, the methods can be useful for preparing target polynucleotide(s) for sequencing by the methods commercialized by Helicos Biosciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058. In other embodiments, the methods can be useful for preparing target polynucleotide(s) for sequencing by the methods commercialized by Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764.

Another example of a sequencing technique that can be used in the methods of the provided invention is semiconductor sequencing provided by Ion Torrent (e.g., using the Ion Personal Genome Machine (PGM)). Ion Torrent technology can use a semiconductor chip with multiple layers, e.g., a layer with micro-machined wells, an ion-sensitive layer, and an ion sensor layer. Nucleic acids can be introduced into the wells, e.g., a clonal population of single nucleic can be attached to a single bead, and the bead can be introduced into a well. To initiate sequencing of the nucleic acids on the beads, one type of deoxyribonucleotide (e.g., dATP, dCTP, dGTP, or dTTP) can be introduced into the wells. When DNA polymerase incorporates one or more nucleotides, protons (hydrogen ions) can be released in the well, which can be detected by the ion sensor. The semiconductor chip can then be washed and the process can be repeated with a different deoxyribonucleotide. A plurality of nucleic acids can be sequenced in the wells of a semiconductor chip. The semiconductor chip can comprise chemical-sensitive field effect transistor (chemFET) arrays to sequence DNA (for example, as described in U.S. Patent Application Publication No. 20090026082). Incorporation of one or more triphosphates into a new nucleic acid strand at the 3' end of the sequencing primer can be detected by a change in current by a chemFET. An array can have multiple chemFET sensors.

Another example of a sequencing technique that can be used in the methods of the provided invention is nanopore sequencing (see e.g. Soni G V and Meller A. (2007) Clin Chem 53: 1996-2001). A nanopore can be a small hole of the order of 1 nanometer in diameter. Immersion of a nanopore in a conducting fluid and application of a potential across it can result in a slight electrical current due to conduction of ions through the nanopore. The amount of current that flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore can represent a reading of the DNA sequence.

Genetic Analysis

The methods of the present invention can be used in the analysis of genetic information of selective genomic regions of interest as well as genomic regions that can interact with the selective region of interest. Amplification methods as disclosed herein can be used in the devices, kits, and methods known to the art for genetic analysis, such as, but not limited to those found in U.S. Pat. Nos. 6,449,562, 6,287,766, 7,361,468, 7,414,117, 6,225,109, and 6,110,709. In some cases, amplification methods of the present invention can be used to amplify target nucleic acid of interest for DNA hybridization studies to determine the presence or absence of polymorphisms. The polymorphisms, or alleles, can be associated with diseases or conditions such as genetic disease. In other cases the polymorphisms can be associated with susceptibility to diseases or conditions, for example, polymorphisms associated with addiction, degenerative and age related conditions, cancer, and the like. In other cases, the polymorphisms can be associated with beneficial traits such as increased coronary health, or resistance to diseases such as HIV or malaria, or resistance to degenerative diseases such as osteoporosis, Alzheimer's or dementia.

Digital Measurements

The methods of the present invention can be used in the digital analysis of gene expression, gene expression patterns associated with disease, including diagnosis, prognosis and detection as well as identifying genetic disorders, e.g., chromosomal or gene translocations, deletions, duplications and defects as well as studying selective genomic regions of interest and genomic regions that can interact with the selective region of interest. In some embodiments, determination of Digital Gene Expression (DGE) or Copy Number Variation (CNV) digital measurements can be achieved by quantitating the number of gene reads within the total number of reads. In some embodiments, paired end sequencing can be performed. Sequencing can be performed via high throughput sequencing on a variety of platforms as is known to one of skill in the art. In some embodiments, the sequencing data/reads are mapped to the genome/transcriptome (for cDNA). In some embodiments, sequence data can be evaluated to remove duplicate reads. In some embodiments, probe sequences are counted for the number of times they appear in de-duplicated sequence dataset as a measure of the number of copies of the original nucleic acid molecules present in the starting sample.

In some embodiments, verification of a probe correctly annealing to its complementary probe target region within the specific nucleic acid can be evaluated. In one embodiment, evaluation of probe properly annealing can be done by paired end alignment, if both ends, forward read and reverse read align as expected, the probe is counted. In some embodiments, evaluation of probe properly annealing can be done by examining the probe sequence+20 bases sequenced of the specific nucleic acid 3' of the probe sequence and use the forward read only for duplication analysis. If probe+20 aligns, the probe was in the desired location.

An advantage of using probe sequence counts rather than random sequence is the simplification of copy number analysis because the same sequences are used across different samples for each measurement. Probe counting allows for high sample throughput via multiplex sequencing (e.g., at least 96 samples per sequencing run). Targeted RNA-sequencing can provide a high level of focus for RNA-sequencing analysis, as greater than 90% of reads are derived from targeted genes while extending the ability to target coding or noncoding genes, specific exons, UTRs, RNA isoforms and gene fusions. Probe counting can also reduce bias of exon usage, transcript size and sequence dependent amplification/sequencing and allow for removal of PCR duplicates.

The digital analysis can be performed by determining PCR duplicates prior to quantitation. Such an analysis, using illumina sequencing technology, is illustrated in FIGS. 6A-6C and with reference to FIG. 1. Briefly, the forward read, illustrated for gDNA (FIG. 1), as shown in FIG. 6A includes a forward priming site 12 utilized by a forward primer 30 sequencing at least 1, at least 2, at least 3, at least 4, at least 5, at least 6, at least 7, at least 8, at least 9, at least 10, at least 15, at least 20, at least 25, at least 30, at least 35 and so on base sequences of a forward sequence 32 that extends into the specific nucleic acid 10 sequence and can be used to map forward read sequence 32 to the genome (or transcriptome for cDNA) region. The index read, as shown in FIG. 6B, can indicate the sample origin (e.g., a library barcode common with the library). The index read starts at the index priming site 18 with index primer 34 and includes the sequenced at least 1, at least 2, at least 3, at least 4, at least 5, at least 6, at least 7, at least 8, at least 9, at least 10 and so on bases of the index bases (e.g., barcode sequence) 16 and n-random bases 14, yielding index read 36. In some embodiments, the forward read sequence 32 in combination with indexing read base sequence and N~ random bases 36 are unique to the ligation event for each specific nucleic acid sequence. In some embodiments, the combination of the forward read sequence 32 start site genome (transcriptome for cDNA) coordinates plus index read sequence 36 N-random bases 14 can be used to determine PGR duplicates for each probe extension product 21 or 22 and thus the corresponding specific nucleic acid sequence 10 or 9 having probe target region 50 or 60. The reverse read 44, as illustrated in FIG. 6C verities the probe annealed to the correct genome/transcriptome position and thus to its complementary probe target region. Flow cell sequences 33 and 35 are appended at the ends of the probe extension product during enrichment.

The digital analysis can be performed by determining PGR duplicates prior to quantitation. Such an analysis, is illustrated in FIGS. 8A-8C and with reference to FIG. 1 and FIG. 5. The read having the probe sequence 44, (FIG. 5) as illustrated in FIG. 8A verifies the probe annealed to the correct genome/transcriptome position and thus to its complementary probe target region. The read having the probe sequence comprises a 15 base linker 38, a 40 base oligonucleotide gene specific sequence 50 or 60 (probe target region) and an X-base (e.g., 10 base) of region 10 about 10 bases 3' to the 40 base oligonucleotide gene specific sequence 50 or 60 as represented in a genome (or transcriptome) database. The read having the specific nucleic acid sequence 10, illustrated for gDNA (FIG. 1), as shown in FIG. 8B includes a priming site 12 utilized by primer 30 sequencing at least 1, at least 2, at least 3, at least 4, at least 5, at least 6, at least 7, at least 8, at least 9, at least 10, at least 15, at least 20, at least 25, at least 30, at least 35 and so on base sequences of sequence 32 (FIG. 5) that extends into the specific nucleic acid 9 or 10 sequence and can be used to map read having the specific nucleic acid sequence 32 to the genome (or transcriptome for cDNA) region. The sequence read comprising the index sequence and N6 sequence, as shown in FIG. 8C, can indicate the sample origin (e.g., a library barcode common with the library). The index read primer 34 anneals to the index priming site 18 producing read sequence 36 comprising at least one of the sequenced at least 1, at least 2, at least 3, at least 4, at least 5, at least 6, at least 7, at least 8, at least 9, at least 10 and so on bases of the index bases (e.g., barcode sequence) 16 and n-random bases 14, yielding sequencing read 36. In some embodiments, the read having the specific nucleic acid sequence (FIG. 8A) would verify specificity of the probe annealing to the probe target region. In some embodiments, the read having the specific nucleic acid sequence are binned into a probe target sequence database and the e.g., 10 bases of specific nucleic acid sequence 9 or 10 would need to align within a unique probe bin and in so matching verify specificity of the probe annealing to its probe target region. In some embodiments, the read having the specific nucleic acid sequence would be compared with about 10 base oligonucleotide matches determined if the sequence is unique within the bin. Common reads would then be compared to the corresponding N6 with identical N6 reads being collapsed together as a single entry and only counted once. In some embodiments, the read having at least one of the index read and the N6 read can be about 14 bases in length. In some embodiments, the read having the specific nucleic acid sequence can be about 10 bases. In some embodiments, the read having the probe sequence can be about 65 bases (about 15 bases for the linker sequence, about 40 bases for the probe target region (gene specific sequence as represented in a genome/transcriptome), and about 10 bases 3' to the probe target region. In some embodiments, a look up table can be used. In some embodiments, the probe sequences are counted. In some embodiments the N6 sequence designates duplicates for elimination.

In some embodiments, read sequence 32 in combination with read sequence 36 are unique to the ligation event for each specific nucleic acid sequence. In some embodiments, the combination of read sequence 32 start site genome (transcriptome for cD'NA) coordinates plus read sequence 36 N-random bases 14 can be used to determine PGR duplicates for each probe extension product 22 or 21 and the corresponding specific nucleic acid sequence 10 or 9 having probe target region 50 or 60. In some embodiments, read sequence 44, as illustrated in FIG. 6C verifies the probe annealed to the correct genome/transcriptome position and also to its complementary probe target region 50 or 60.

Figure 6:
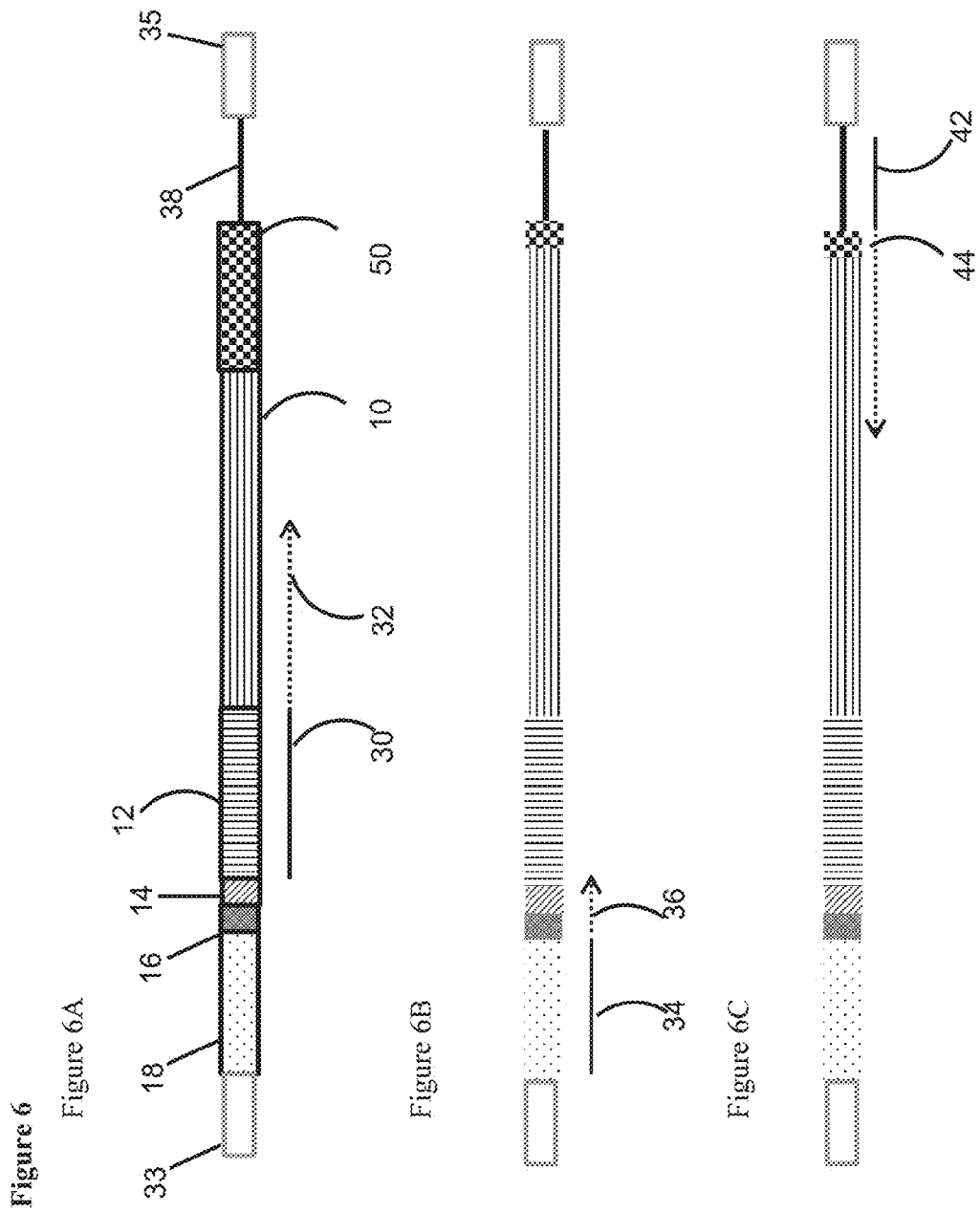
FIG. 6 illustrates embodiments disclosed herein for removing duplicate reads from sequencing data.

In some embodiments, the duplicate reads are removed prior to DGE or CNV quantitation as disclosed above. The probe sequences that are correctly mapped in the genome/transcriptome are then counted. In some embodiments DGE or CNV can be determined by the counts of each probe sequence. In some embodiments, probe counts can be combined by, e.g., averaging counts across probes over the length of a gene. In some embodiments, read counts can be normalized between samples, e.g., read counts normalized as a percentage of total reads. In some embodiments, read counts can be normalized by e.g., normalizing total read counts before counting each probe sequence. In some embodiments, read counts can be normalized by the number of reads aligned to the genome or reads derived from the probe target region, As illustrated in FIG. 5 the structure of the sequencing library and identification of sequencing reads provides for multiplex quantitation using high throughput sequencing methods. As illustrated in FIG. 7A. with reference to FIG. 6, forward primer 30 can be complementary to the forward read 1 priming site 12 and the read can be extended 32 into the specific nucleic acid 10 (gDNA) or 13 (cDNA) sufficiently to map the read to the genome or transcriptome. Additionally, an index read sequence illustrated in FIG. 7B, can be read from the "index priming site" 18 using complementary primer 34 and reading 36 into "index bases" 16 and "n-random bases" 14, Additionally, a "reverse read sequence" can be determined (FIG. 5, FIG. 6 and FIG. 7C). The reverse sequence primer 42 hybridizes to the "reverse read priming site" 38 and reads 44 through the probe 50 or 60 (gDNA or cDNA, respectively, FIG. 1, FIG. 2, illustrated in FIG. 6) (probe target region site) and at least 1, at least 2, at least 3, at least 4, at least 5, at least 6, at least 7, at least 8, at least 9, at least 10 and so on adjacent bases 10 (gDNA) or 13 (cDNA) to verify if the probe extension product 22 or 21 (gDNA or cDNA, respectively, FIG. 1, FIG. 2) was the product of the probe hybridizing to the correct genome or transcriptome. Probe sequences that are correctly mapped in the genome or transcriptome are counted. DGE or CNV can be determined by the counts of each probe sequence and/or probe counts can be combined, including but not limited to, with averaging counts across probes over the length of a gene corresponding to the specific nucleic acid sequence. The read counts can be normalized between samples. In some embodiments, read counts can be normalized between samples, e.g., read counts normalized as a percentage of total reads. In some embodiments, read counts can be normalized by e.g., normalizing total read counts before counting each probe sequence. In some embodiments, read counts can be normalized by the number of reads aligned to the genome or reads derived from the probe target region. Other methods for normalization are well known to one of skill in the art of NGS sequence analysis.

Figure 9:
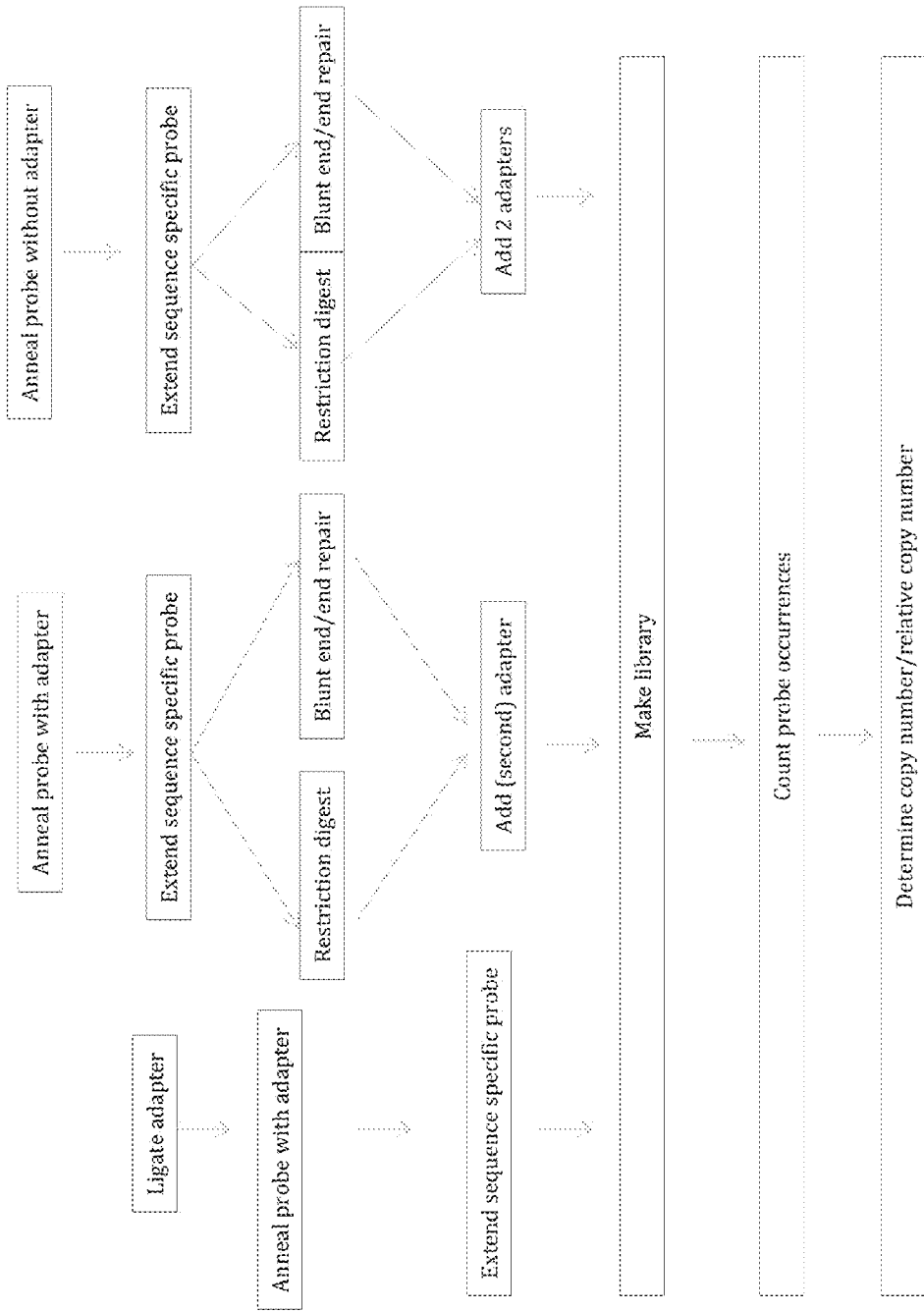
FIG. 9 graphically illustrates embodiments disclosed herein for generation of sequencing libraries and subsequent digital quantification.

FIG. 9 provides a graphical illustration of the construction of sequencing libraries generated for digital analyses.

Figure 10:
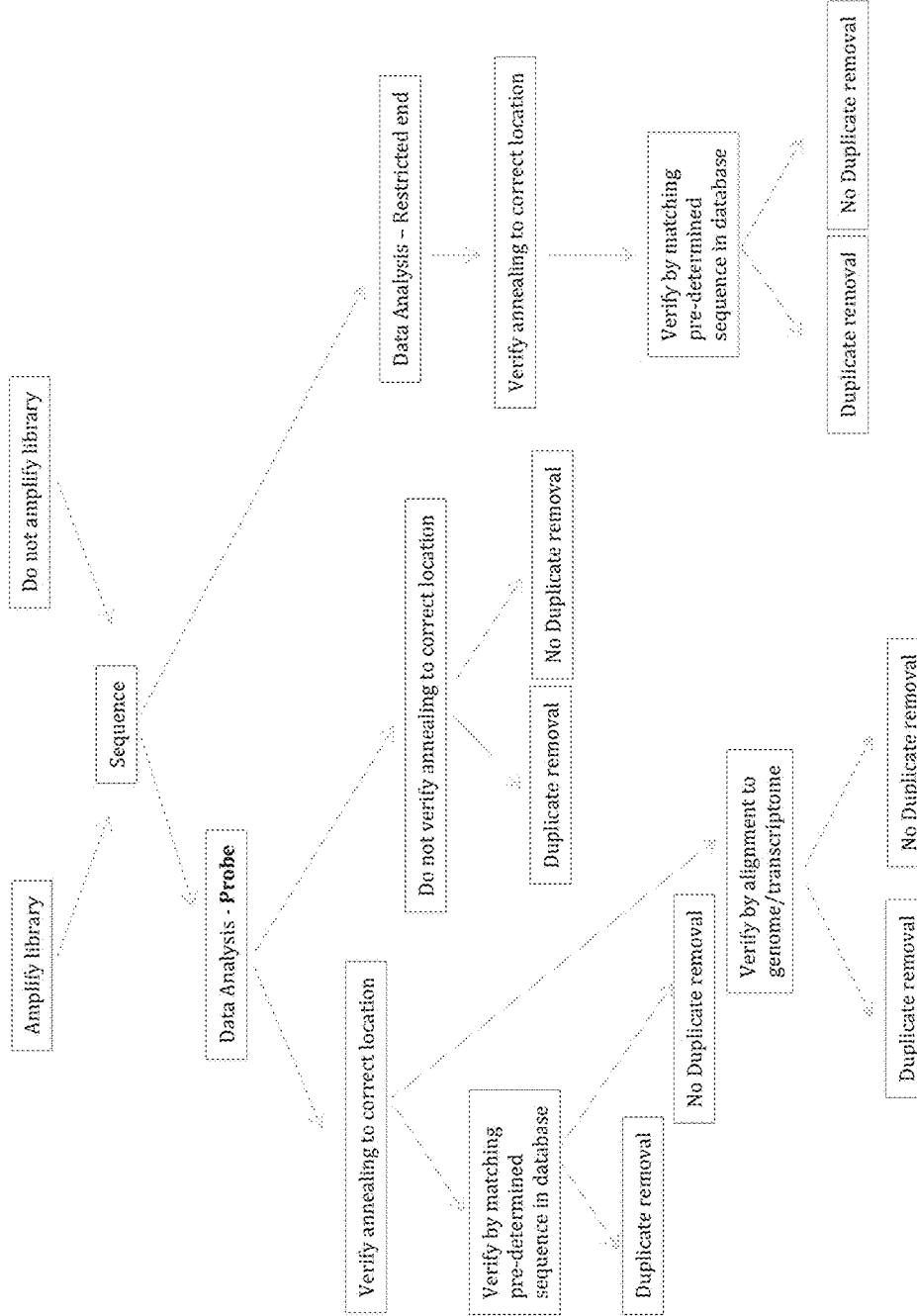
FIG. 10 graphically illustrates embodiments disclosed herein for using a sequencing library for NGS sequencing and analyzing sequence data for digital quantification.

FIG. 10 provides a graphical illustration for the analyses of sequencing data generated from sequencing libraries constructed as illustrated in FIG. 9.

In some embodiments, the methods of the disclosed invention can be used for digital measurements to analyze gene expression characteristics and properties of, for example, but not limited to, a tissue, a tumor, a circulating cell, as well as to compare diseased verses non-diseased patients, and a patient's normal verses diseased tissue. In some embodiments, the methods of the disclosed invention can be used for copy number variation (CNV) digital quantitation. CNV can indicate DNA alterations within a genome resulting in a cell having an abnormal or a normal variation in the number of copies of DNA sections. CNVs can identify deletion of a large region of a genome resulting in fewer than normal number or duplication of a large region of a genome having more than the usual number within a chromosome. There are associations between CNVs and susceptibility or resistance to disease. Such measurements can be useful for diagnosis, disease staging, prognosis, determining disease progression, viral load, as well as the impact of gene expression or CNV on a therapeutic agent's efficacy or efficiency and the like as would be known to one of skill in the art.

In another aspect, disclosed is a composition comprising the first nucleic acid fragment sequence amplified by the disclosed method. In some embodiments, the first nucleic acid fragment or non-fragmented nucleic acid sample can be from a human sample selected from a same human: a single cell, a non-diseased tissue, a diseased tissue, a FFPE sample or a fresh-frozen sample, a tissue, an organ, a tumor, a specimen of an organic fluid taken from a patient, freely circulation nucleic acid, a fungus, a prokaryotic organism and a virus. In some embodiments, the second nucleic acid fragment or non-fragmented nucleic acid sample can be from a sample selected from the same human having tissue which can be either a diseased tissue or a non-disease tissue, can be collected on a same day, can be collected on separate days, can be collected from different samples, can be collected from samples prepared by different methods or can be collected from samples by different purification methods and combinations thereof. In some embodiments, the first nucleic acid fragment or non-fragmented nucleic acid sample comprising the first adaptor sequence can be further enriched and prepared for massively parallel sequencing. In some embodiments, the first nucleic acid fragment or non-fragmented nucleic acid sample can be double stranded. In some embodiments, the first adaptor sequence can be appended to a 5' end of said first nucleic acid fragment or non-fragmented nucleic acid sample. In some embodiments, the first adaptor sequence comprises a restriction and/or cleavage site for a nucleic acid modifying enzyme.

In yet another aspect, a disclosed method can have a second human nucleic acid fragment or second non-fragmented nucleic acid sample with an adaptor. In some embodiments, the second human sample can be derived from a different human than the human from whom the first nucleic acid sample was derived. In some embodiments, the second nucleic acid fragment or second non-fragmented nucleic acid sample can be a sample selected from the same human having tissue which can be either a diseased tissue or a non-disease tissue, can be collected on a same day, can be collected on separate days, can be collected from different samples, can be collected from samples prepared by different methods or can be collected from samples by different purification methods and combinations thereof. In some embodiments, the second nucleic acid fragment or second non-fragmented nucleic acid sample can be a sample selected from a different human having tissue which can be either a diseased tissue or a non-disease tissue, can be collected on a same day, can be collected on separate days, can be collected from different samples, can be collected from samples prepared by different methods or can be collected from samples by different purification methods and combinations thereof.

In a further aspect, disclosed is a method for quantitating a second human nucleic acid according to previously disclosed the methods.

Kits

Any of the compositions described herein can be included in a kit. In a non-limiting example the kit, in suitable container means, comprises: one adapter with a known sequence, one probe having a sequence specific portion and common portion of known sequence, one forward primer having a direct partial complement to the at least either the adaptor or probe common portion and one reverse primer having a direct partial complement to either the adaptor or probe common portion. The kit can further contain additional adapters, primers and/or reagents useful for ligation, target enrichment and library preparation. The kit can further optionally contain a DNA-polymerase. The kit can further optionally contain reagents for amplification, for example reagents useful for PCR amplification methods. The kit can further optionally contain reagents for sequencing, for example, reagents useful for next-generation massively parallel sequencing methods.

The containers of the kits can include at least one vial, test tube, flask, bottle, syringe or other containers, into which a component can be placed, and preferably, suitably aliquoted. Where there is more than one component in the kit, the kit also can contain a second, third or other additional container into which the additional components can be separately placed. However, various combinations of components can be included in a container.

When the components of the kit can be provided in one or more liquid solutions, the liquid solution can be an aqueous solution. However, the components of the kit can be provided as dried powder(s). When reagents and/or components are provided as a dry powder, the powder can be reconstituted by the addition of a suitable solvent.

A kit can include instructions for employing the kit components as well the use of any other reagent not included in the kit. Instructions can include variations that can be implemented.

EXAMPLES

Example I: Differential Expression Levels of Specific Transcripts Between Two Samples Starting with 100 ng total RNA double stranded cDNA was made using cDNA target enrichment module sold under the trademark OVATION by NuGEN according to the manufacturer's recommendation. cDNA samples were added directly into target enrichment kit sold under the trademark OVATION by NuGEN according to manufacturer's directions. Probes used in hybridization were a pool of probes targeting 270 genes The resulting libraries were diluted to 2rA4 and paired end sequencing was performed on the enriched library on an Illumina® MiSeq® DNA Sequencer. The following paired end series was run at 75 bases forward read (111), 75 bases reverse read (R2), 14 base index reads (II).

Data Analysis

Paired end alignments were performed for the forward and reverse sequencing reads and each were mapped to the human genome version hg19 using TopHat Alignment software (v.2.0.10) with default settings. Pairs of reads that did not map to a targeted region were eliminated. Forward reads with the same start coordinate were then evaluated for the index sequence's N6 sequence (n-random sequence). In instances where the N6 sequences were identical, then the reads were marked as duplicates and only one read of the group was retained as being derived from a single distinct nucleic acid molecule. The identified duplicate reads were marked and then removed. After filtering for on target and deduplicated read pairs, the filtered reverse read sequences were trimmed to remove adaptor and linker sequences using Trimgalore (v.0.3.1), and shortened to the first 35 bases using FASTX Trimmer software. Trimmed reverse read sequences were then mapped to a probe sequence file (provided with the probes used) containing the sequences of the targeting oligonucleotide using Bowtie Alignment software (v. 1.0.0) with default parameters and '-norc' to prevent reverse complement matching. Aligned reverse reads were associated with their originating primer and counted. The number of times each probe was detected was a measure of the number of times the specific transcript was present in the original sample. Table 1 illustrates DGE data in which the read counts were normalized between samples.

TABLE 1

Representation of gene expression of three genes between two cancer cell lines

| Gene | Normalized Probe Reads UHR | Normalized Probe Reads H2228 | Ratio UHR/H2228 |
|---|---|---|---|
| CCND3 | 499 | 494 | 1.01 |
| TAF15 | 541 | 1074 | 0.52 |
| PBX1 | 118 | 23 | 5.13 |

As depicted in Table 1, a mixed cancer cell line RNA sample (UHR, Universal Human Reference RNA) has a relatively low level of expression of genes TAF15 compared to H2228 cells (adenocarcinoma; non-small cell lung cancer). Both cell types have very similar expression levels of CCND3. Conversely UHR has higher expression of PBX1 compared to H2228.

Example II

Differential Expression Levels of Specific Transcripts Between Two Samples Without Genome AlignmentStarting with 100 ng total RNA double stranded cDNA is made using cDNA target enrichment module sold under the trademark OVATION by NuGEN, according to the manufacturer's recommendation. cDNA samples are added directly into the target enrichment kit sold under the trademark OVATION by NuGEN according to manufacturer's directions. Probes used in hybridization are a pool of probes targeting 270 genes, such as the target enrichment module sold under the trademark OVATION by NuGEN.

The resulting libraries are diluted to 2 nM and paired end sequencing is performed on the enriched library on an Illumina® MiSeq® DNA Sequencer. The following paired end series is run at 75 bases forward read (R1), 75 bases reverse read (R2), 14 base index reads (II).

Data Analysis

Reverse read sequences are trimmed with a pattern match at the 5' end for 15 bp linker sequence and 0-3 bases of diversity sequence. After linker trimming the first 40 bp of the reverse read are constructed into a Burrows-Wheeler transform (BWT) to match tiled probe 12-mers in each read using BEETL software (version 1.1.0, github.com/BEETL/BEETL). Each read pair is then labeled as being derived from the probe with the most 12-mer matches to the reverse read. Labeled read pairs are then deduplicated per-probe, by analyzing the index sequence's N6 sequence (n-random sequence) along with the first 10 bases of the Forward read. In instances where the reads are derived from the same probe, the N6 sequences are identical, and the first 10 bases of the forward read are the same, then the reads are marked as duplicates and only one read of the group was retained as being derived from a single distinct nucleic acid molecule. After filtering for deduplicated read pairs, a total deduped read count was obtained for each probe. The number of times each probe was detected was a measure of the number of times the specific probe was present in the original sample. Counts per probe are then averaged to obtain counts per gene based on the probe annotation file, as a measure of relative abundance for that gene in the particular sample.

Example III: Differential Expression of Specific Transcripts Mapping Forward Reads Starting with 100 ng total RNA input from Universal Human Reference Sample (UHR) double stranded cDNA was made using the cDNA target enrichment module sold under the trademark OVATION by NuGEN according to the manufacturer's recommendation. cDNA samples were added directly into the target enrichment kit sold under the trademark OVATION by NuGEN according to manufacturer's directions. A control library starting with 100 ng DNA input from Promega Male Reference Sample was also processed using the target enrichment kit sold under the trademark OVATION by NuGEN according to the manufacturer's recommendation. Probes used in hybridization were a pool of probes targeting 95 genes.

The resulting libraries were diluted to 2 nM and paired end sequencing was performed on the enriched library on an Illumina® MiSeq® DNA Sequencer. The following paired end series was run at 70 bases forward read (R1), 88 bases reverse read (R2), 14 base index reads (II).

Data Analysis

For both RNA and DNA derived data forward reads were quality trimmed and trimmed of linker and adaptor sequences. For DNA derived data, forward reads were mapped to the human genome version hg19 using Bowtie Alignment software with –m 2 parameter. For RNA derived data, forward reads were first mapped to ribosomal RNA reference using STAR Alignment software, reads that were unmapped to ribosomal RNA were then mapped to the human version hg19 also using STAR Alignment software. After alignment, forward reads for both the RNA and DNA data with the same start coordinate were then evaluated for the index sequence's N6 sequence (n-random sequence). In instances where the N6 sequences were identical, then the reads were marked as duplicates and only one read of the group was retained as being derived from a single distinct nucleic acid molecule. The identified duplicate reads were marked and then removed. CoverageBed software with default settings was then used to count deduplicated forward reads overlapping any portion of each target region (exons) for each dataset. The counts for each target region were normalized for total reads in all target regions of the dataset and then target regions corresponding to each exon within a gene were averaged for a normalized gene count for the DNA and RNA data. The DNA counts are expected to be quite even as expression levels do not affect the probe's ability to generate reads. The RNA counts are expected to have variability due to expression level changes. Based on that idea, the log 2 ratio of normalized counts RNA/DNA was then computed as a measure of gene abundance in the RNA. A students T-test was then used to compute a p-value for each gene measurement. Genes with a p-value<0.05 and a log ratio >0 were noted as upregulated genes and genes with a p-value<0.05 and a log ratio <0 were noted as downregulated genes.

Figure 11A:
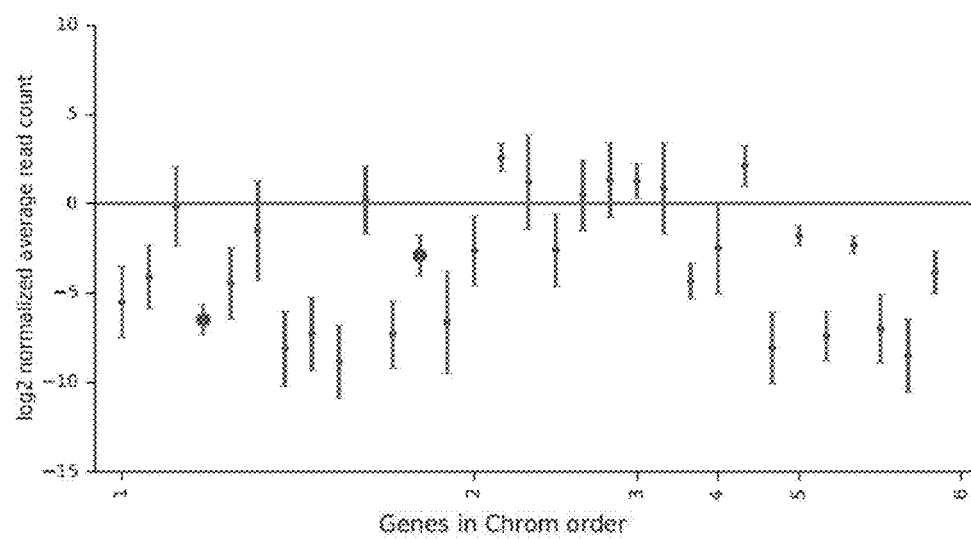
FIG. 11A, FIG. 11B, and FIG. 11C graphically illustrate the plot of gene abundance at the RNA level in a panel of 95 genes in chromosomal order. Genes colored with a dot and appearing below the zero-value line are significantly downregulated, and genes colored with a dot and appearing above the zero-value line are significantly upregulated. Error bars reflect the standard deviation in both the DNA and RNA data.
Figure 11B:
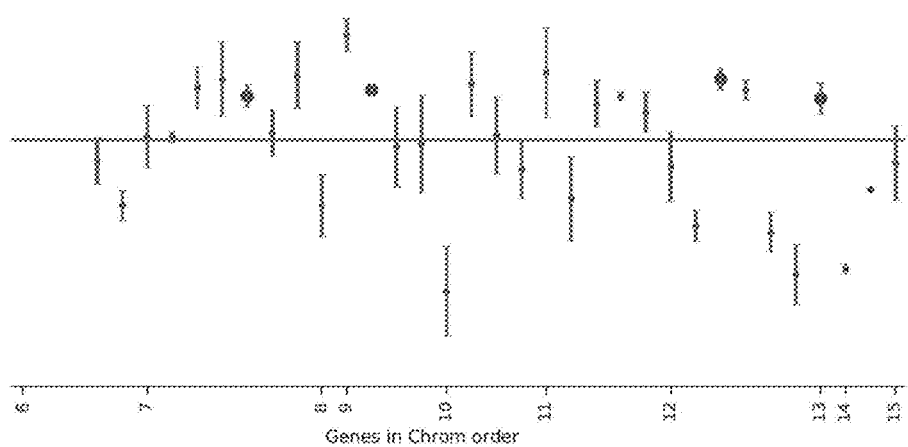
Figure 11C:
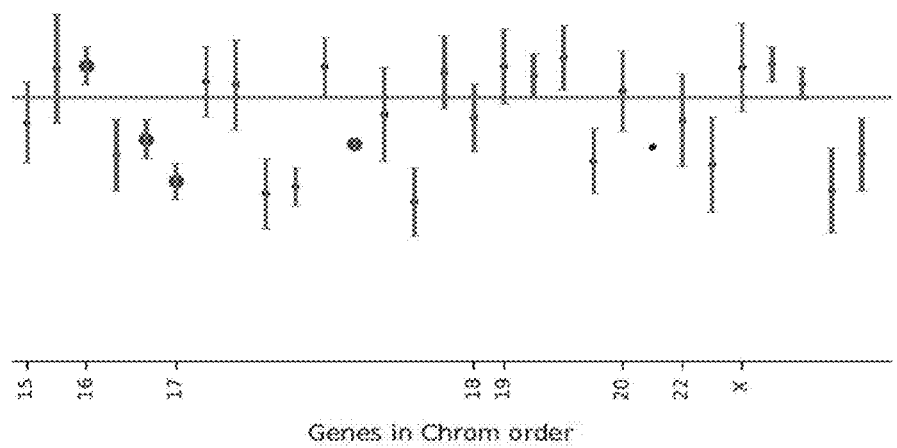
Figure 12A:
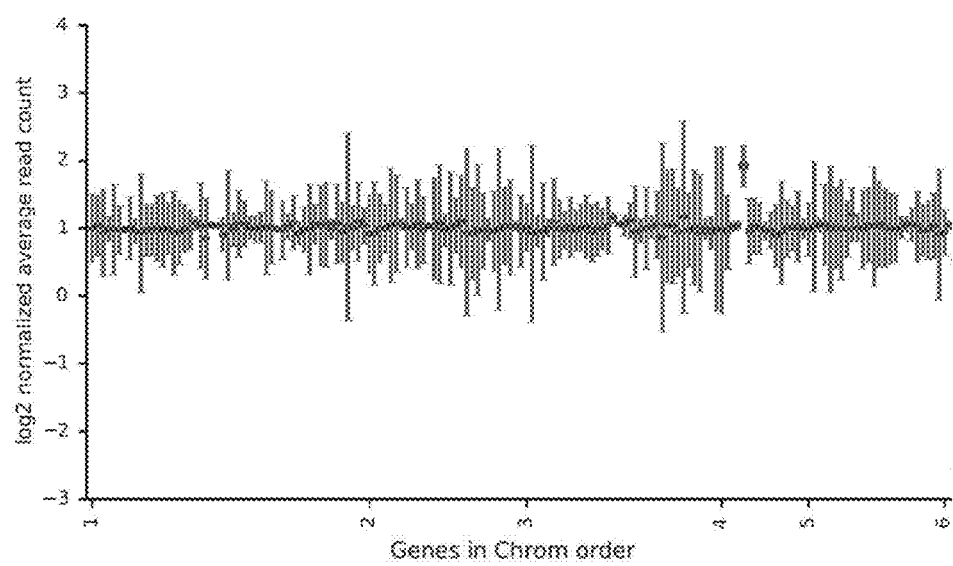
FIG. 12A, FIG. 12B, and FIG. 12C graphically illustrate the plot of measured levels for all genes in the 509 gene panel sorted in chromosomal order. Genes with copy number changes are colored with a dot and appear above the one-value line. Error bars are reflective of combined variation in the probe counts of the sample and control datasets.
Figure 12B:
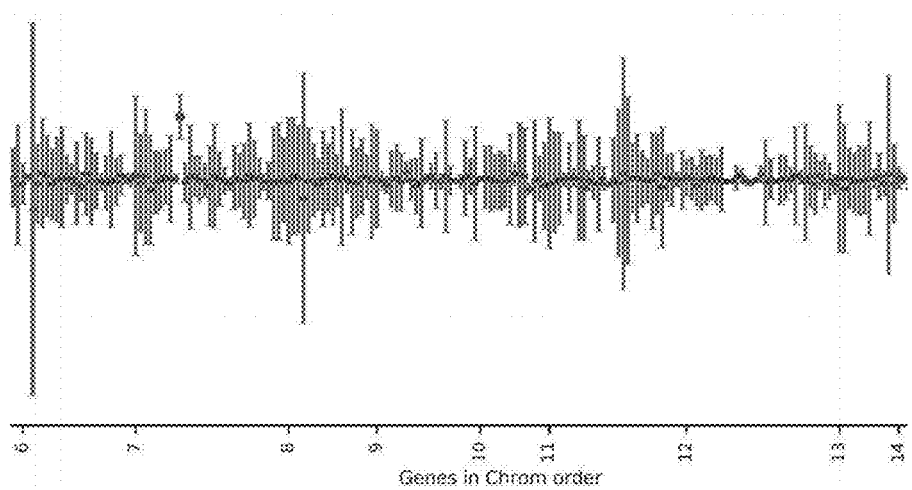
Figure 12C:
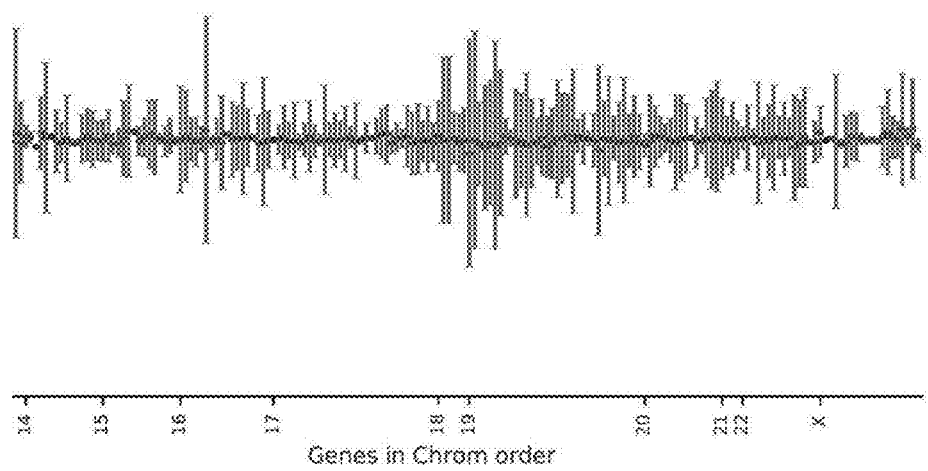

Table 2 depicts five genes that were significantly upregulated and five genes that were significantly downregulated from the plot all gene abundance at the RNA level in the panel of 95 genes in chromosomal order (FIG. 11).

TABLE 2

Relative abundance of significantly changed genes.

| Direction | Gene | Chromosome | Abundance | P-Value |
|---|---|---|---|---|
| Up | GUSB | 7 | 6.291068 | 3.18E−04 |
| Up | ANXA1 | 9 | 8.132735 | 3.37E−07 |
| Up | ITGB7 | 12 | 13.091 | 5.98E−05 |
| Up | GAS6 | 13 | 5.678613 | 2.64E−04 |
| Up | TSC2 | 16 | 3.440623 | 3.22E−04 |
| Down | AMPD1 | 1 | 0.011096 | 2.95E−06 |
| Down | CR2 | 1 | 0.133867 | 3.35E−04 |
| Down | ITGAX | 16 | 0.194365 | 2.39E−06 |
| Down | NOS2 | 17 | 0.037126 | 9.74E−07 |
| Down | ITGA2B | 17 | 0.15729 | 2.31E−13 |

Example IV: Relative Expression Levels of Specific Transcripts Using Forward Reads Starting with 100 ng total RNA double stranded cDNA is made using the cDNA target enrichment module sold under the trademark OVATION by NuGEN according to the manufacturer's recommendation. An adapter corresponding to the ILMN reverse flow cell sequence is ligated onto the 5' end of each cDNA fragment. Probes containing a sequence specific region followed by a 15 base linker and a XX base sequence corresponding to the ILMN forward flow cell sequence are annealed to the target and extended with a DNA polymerase. DNA fragments containing both forward and reverse flow cell sequences are amplified by PCR under conditions and with reagents recommended and provided by NUGEN.

The resulting libraries are diluted to 2 nM and paired end sequencing is performed on the enriched library on an Illumina® MiSeq® DNA Sequencer. The following paired end series is run at 70 bases forward read (R1), and 14 base index reads (II).

Data Analysis

Forward reads sequences are trimmed to remove linker sequences using Trimgalore software (v.0.3.1), and shortened to the last 55 bases using FASTX Trimmer software. Trimmed forward reads are mapped to the human genome version hg19 using Bowtie Alignment software with −m 2 parameter. Reads that do not map to a targeted region are eliminated. Reads are identified that map to the same start coordinates in the genome. Reads with the same start coordinates are then evaluated for the index sequence's N6 sequence (n-random sequence). In instances where the N6 sequences are identical, then the read pairs are marked as duplicates and only counted as being derived from a single distinct nucleic acid molecule. The identified duplicate reads are marked and then removed. Remaining reads are mapped to a probe sequence file (provided with the probes used) containing the sequences of the targeting oligonucleotide using Bowtie Alignment software (v. 1.0.0) with default parameters and norc' to prevent reverse complement matching. The number of times each probe is detected is a measure of the number of times the specific transcript is present in the original sample. Reads overlapping any portion of the target region (exons) are counted. The counts corresponding to each exon within a gene are averaged. If any exon has counts below 2 standard deviations of the average, that exon is dropped and the average recalculated.

Example V: Determination of Copy Number Variation (CNV) by DNA Sequencing

Two human gDNA samples, one derived from a trisomy chromosome 13 male and another a disomy chromosome 13 female were fragmented to approximately 500 bp length by sonication with a Covaris system. 100 ng of 500 bp fragments of gDNA from each sample were added to the target enrichment kit sold under the trademark OVATION by NuGEN according to manufacturer's directions. Probes used in hybridization were a pool of probes targeting 344 genes, such as the cancer panel target enrichment system sold under the trademark OVATION by NuGEN.

The resulting libraries were diluted to 2 nM and paired end sequencing was performed on the enriched library on an Illumina® MiSeq® DN A Sequencer. The following paired end series was run at 75 bases forward read (R1), 88 bases reverse read (R2), 14 base index read (II).

Data Analysis

Data were analyzed by two independent methods; removing duplicates and not removing duplicates. Briefly, forward reads were aligned to the human genome version hg19 using Bowtie Alignment software (v. 1.0.0) with default settings. If any forward reads were determined to align to the same genomic start coordinate, the corresponding index read was examined. In instances where the index Read sequences corresponding to those forward reads with the same genomic start coordinates were identical, the reads were marked as duplicates and only counted as a single distinct nucleic acid molecule. Reverse reads corresponding to the remaining distinct forward reads were aligned using Bowtie to the sequences in a Probe Database. Aligned reverse reads were binned and counted according to which probe sequence they represent. The number of times each probe was represented was a measure of the number of times the starting specific nucleic acid molecule was present in the original sample.

Alternatively, representation was established without removing duplicate reads by cataloging the 40 base reverse reads according to sequences present in the Probe Database. The number of reads aligning to each representative in the probe reference database was determined. Reads that did not match sequences in the database were disregarded. The number of times each probe was detected was a measure of the number of times the specific sequence was present in the original sample. Table 3 depicts CNV data using either method described above in which the read counts were normalized to total sequencing read number and any counts below 10 were removed from analysis. The ratio of the probe count for a given probe in a trisomy male sample to the counts of the same probe in a wild type female sample were averaged for all probes on a given chromosome.

TABLE 3

Copy number variation data from a trisomy 13 male in which read counts were normalized to total sequencing read numbers

| Chromosome | No duplicate removal Average probe count ratio | Duplicates removed Average probe count ratio |
|---|---|---|
| chr 1 | 1.002485 | 0.990606365 |
| chr 2 | 1.025382 | 1.010290049 |
| chr 3 | 1.028736 | 1.016439439 |
| chr 4 | 1.045166 | 1.032544903 |
| chr 5 | 1.002378 | 0.998957554 |
| chr 6 | 1.015266 | 0.997262904 |
| chr 7 | 1.022412 | 1.021639631 |
| chr 8 | 1.046251 | 1.028980962 |
| chr 9 | 1.009415 | 0.991277289 |
| chr 10 | 1.035216 | 0.993768193 |
| chr 11 | 1.01177 | 1.00377304 |
| chr 12 | 1.027063 | 1.004790487 |
| chr 13 | 1.485411 | 1.471641235 |
| chr 14 | 0.996186 | 0.986919321 |
| chr 15 | 0.986867 | 0.981480187 |
| chr 16 | 0.967682 | 0.964463441 |
| chr 17 | 0.999821 | 0.992014077 |
| chr 18 | 1.035764 | 1.016860381 |
| chr 19 | 0.967125 | 0.958202381 |
| chr 20 | 1.012836 | 1.010031227 |
| chr 21 | 1.00104 | 1.013150115 |
| chr 22 | 0.975676 | 0.972111601 |
| chrX | 0.548004 | 0.54329808 |

As depicted in Table 3, a diploid male has a single X-chromosome vs. a diploid normal (wild type, WT) female having two X-chromosomes which is identified by the 0.54 ratio (or 0.55 when duplicates are not removed) of probe counts on the X chromosome. Likewise, both the male and female can have comparable normalized counts for all other chromosomes with the exception of chromosome 13. The trisomy 13 male has an extra chromosome 13 as interpreted by the 1.47 probe count ratio (or 1.49 when duplicates are not removed) establishing a chromosome 13 copy number variation verses comparison to the WT female.

Example VI: Determination of Copy Number Variation (CNV) in Cancer Cell Line by DNA Sequencing Two human gDNA samples, one derived from a pool of normal male (Promega), and the other derived from that same pool of normal male with two extra copies of EGFR and KIT genes spiked in for a total of 4 copies each (previously validated by qPCR) were fragmented to approximately 500 bp length by sonication with a Covaris system. 100 ng of 500 bp fragments of gDNA from each sample were added to the target enrichment kit sold under the trademark OVATION by NuGEN according to manufacturer's directions. Probes used in hybridization were a pool of probes targeting 509 genes, such as the cancer panel target enrichment system sold under the trademark OVATION by NuGEN.

The resulting libraries were diluted to 2 nM and paired end sequencing was performed on the enriched library on an Illumina® MiSeq® DNA Sequencer. The following paired end series was run at 70 bases forward read (R1), 88 bases reverse read (R2), 14 base index read (II).

Data Analysis

For both datasets, forward reads in fastq format are trimmed of linker sequence and low quality bases with Trim Galore software. The reads were aligned to the human genome reference version hg19 using Bowtie Alignment software (v 1.0.0) allowing for reads to map to up to 2 places and picking only a single best alignment (−m 2—best). Aligned reads were subsequently deduplicated using the deduplication software sold under the trademark NUDUP by NuGEN (github.com/nugentechnologies/nudup). For deduplication, if any reads are determined to align to the same genomic start cobiolabordinates the corresponding index read is examined. In instances where the index read sequences corresponding to those forward reads with the same genomic start position were identical, the reads are marked as duplicates and only a single read with the best quality from the set is maintained.

The probes used in the enrichment experiment are expected to produce reads that land within the starting coordinate of the probe to approximately 300 bp downstream of the probe. For all probes in the enrichment, the probe landing zone is defined in a bed file as "probePlus300". The number of deduplicated reads within each probePlus300 region are counted using BEDtools coverageBed. For each probePlus300 region absolute counts are normalized by the total deduplicated reads falling in all probePlus300 regions (sum of all probePlus300 region counts) in order to compare counts across experiments. Next, for each gene, or genomic region, probePlus300 counts are averaged. Normalized average probePlus300 counts for each gene from the cell line sample are compared to the normal blended male sample counts as a ratio. Furthermore, a student's t-test can be used to compute genes or genomic regions where the averaged probePlus300 counts are significantly different for a given gene between the two samples with a multiple hypothesis corrected p-value <0.005.

Table 4 depicts significant copy number changes and p-values in the spike in sample. Specifically, there is only a significant increase in copy number for EGFR and KIT genes—the two genes spiked in at approximately 4 copies.

TABLE 4

Significant copy number changes and p-values in the spike in sample.

| CNV | GENE | Chromosome | Copies | P-Value |
|---|---|---|---|---|
| GAIN | KIT | 4 | 3.790214 | 5.05E−13 |
| GAIN | EGFR | 7 | 4.059194 | 1.62E−16 |

Example VII: Rapid Library Generation for Determination of Copy Number Variation by DNA Sequencing Two human gDNA samples, one derived from a trisomy chromosome 13 male and another a disomy chromosome 13 female can be fragmented to approximately 500 bp length by sonication with a Covaris system, 1 ug of 500 bp fragments of gDNA from each sample can be heat denatured at 95 C for 5 minutes in the presence of probes and probe annealing solution, which may be provided in target enrichment kits sold under the trademark OVATION by NuGEN, and cooled at a rate of 0.1 C per minute to 60 C and held at that temperature for at least 30 minutes. Following the annealing step, a DNA polymerase and deoxynucleotides can be added to the solution to extend probes annealed specifically to their template nucleic acid. This solution can be cooled to room temperature and the unincorporated probes removed by differential bead binding and elution from SPRI beads, consistent with manufacturer's recommendations. The recovered double stranded DNA can undergo end repair and ligation with solutions provided in the target enrichment kit sold under the trademark OVATION by NuGEN.

The resulting libraries can be diluted to 2 nM and paired end sequencing performed on the enriched library on an Illumina® MiSeq® DNA Sequencer. The following paired end series can be run; 75 bases forward read (read 1), 75 bases reverse read (read 2), 14 base index read (read 3).

Data Analysis

Data can be analyzed by cataloging the 75 base reverse reads by sequences present in the Probe Database. The number of reads aligning to each representative in the probe reference database can be determined. Reads that did not align to sequences in the database could be disregarded. The number of times each probe is detected can be a measure of the number of times the specific sequence was present in the original sample. Read counts can be normalized to total sequencing read number and any counts below 10 can be removed from analysis. The ratio of the probe count for a given probe in a trisomy male sample to the counts of the same probe in a wild type female sample can be averaged for all probes on a given chromosome.

Data from this test would reveal the male sample as having a single X-chromosome vs. a diploid normal (wild-type, WT) female having two X-chromosomes and therefore an approximate 0.5 ratio of probe counts on the X chromosome. Likewise, both the male and female would have comparable normalized counts for all other chromosomes with the exception of chromosome 13. The trisomy 13 male has an extra chromosome 13, this would result in a probe count ratio of approximately 1.5 probe count ratio relative to the WT female.

Those having ordinary skill in the art will understand that many modifications, alternatives, and equivalents are possible. All such modifications, alternatives, and equivalents are intended to be encompassed herein.

While the principles of this invention have been described in connection with specific embodiments, it can be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A method for quantitating a plurality of specific nucleic acid molecules comprising:
   a. extending a plurality of probes, wherein each probe is hybridized to a probe target region within a specific nucleic acid molecule within the plurality of specific nucleic acid molecules and each probe has a first adaptor at its 5' end to generate a plurality of extension products;
   b. appending a second adaptor to the double-stranded end of the plurality of probe extension products;
   c. sequencing the plurality of probe extension products to generate sequence data for each of the probe extension products; and
   d. determining the number of each probe that hybridized to a probe target region, wherein the number indicates the quantity of each of the specific nucleic acid molecules comprising the probe target region.

2. A method for quantitating a plurality of specific nucleic acid molecules in a composition comprising:
   a. hybridizing a plurality of probes to a probe target region within a specific nucleic acid molecule, wherein each probe has a first adaptor at its 5' end;
   b. extending each probe to generate a plurality of probe extension products comprising the first adaptor sequence;
   c. appending a second adaptor sequence to the double-stranded end of the plurality of probe extension products;
   d. sequencing the plurality of probe extension products to generate sequence for each of the plurality of probe extension products;
   e. aligning the sequence for each of the plurality of probe extension products to a pre-determined sequence within a probe database, wherein said probe database comprises a plurality of pre-determined sequences, wherein each pre-determined sequence is specific to a probe; and
   f. determining the number of alignments for the sequence of each probe extension product to a pre-determined sequence within the sequencing database, wherein the number of of alignments indicates the quantity of each of the specific nucleic acids molecules to which the probe hybridizes to.

3. The method of claim 2, wherein the composition further comprises a plurality of nucleic acid molecules.

4. The method of claim 2, wherein the sequences of the plurality of probe extension products comprise at least one of a forward read, an index read and a reverse read.

5. The method of claim 3, wherein the sequences of the plurality of probe extension products are mapped to coordinates of a genome or transcriptome to verify intended probe annealing and extension.

6. The method of claim 5, wherein the sequences of the plurality of probe extension products for the forward and reverse reads are mapped for the plurality of specific nucleic acids.

7. The method of claim 3, wherein the sequences of the plurality of probe extension products for the index read identifies at least one of a sample barcode sequence or an n-random sequence.

8. The method of claim 2, wherein following appending of the adaptors the probe extension products are amplified.

9. The method of claim 2, wherein the probe extension product is treated with a restriction endonuclease or undergoes end repair prior to addition of the second adaptor.

10. The method of claim 9, wherein the end repair is blunt end repair.

11. The method of claim 10, wherein the restriction endonuclease treated probe extension product yields a forward read with a common end, and wherein the sequences of the plurality of probe extension products are (i) mapped to coordinates of a genome or transcriptome or (ii) aligned to a reference copy of a probe database transcriptome to verify intended probe annealing.

12. The method of claim 11, wherein reverse read sequences are binned and counted according to which probe sequence they represent, wherein the number of times each probe is represented is a measure of the number of times the starting specific nucleic acid molecule is present in the original sample.

13. The method of claim 11, wherein forward read sequences are binned and counted according to which probe sequence they represent, wherein the number of times each probe was represented was a measure of the number of times the starting specific nucleic acid molecule was present in the original sample.

14. The method of claim 2, wherein the second adaptor sequence comprises at least one of an index sequence priming site, an index nucleotide sequence, an n-random nucleotide sequence, a forward read priming site, a reverse read priming site, and combinations thereof.

15. The method of claim 2, wherein the first adaptor sequence comprises at least one of a forward read priming site, a reverse read priming site and a linker sequence, and combinations thereof.

16. The method of claim 2, wherein the 5' first adaptor is common to each probe extension product.

17. The method of claim 14, wherein the index nucleotide sequence further comprises a barcode sequence.

18. The method of claim 2, wherein the plurality of nucleic acids are derived from a sample selected from the group consisting of a tissue, an organ, a single cell, a tumor, a specimen of an organic fluid taken from a patient, freely circulating nucleic acid, a fungus, a prokaryotic organism and a virus.

* * * * *